US010494407B2

(12) United States Patent
Ensign et al.

(10) Patent No.: US 10,494,407 B2
(45) Date of Patent: Dec. 3, 2019

(54) MOSQUITOCIDAL XENORHABDUS, LIPOPEPTIDE AND METHODS

(71) Applicant: WISCONSIN ALUMNI RESEARCH FOUNDATION, Madison, WI (US)

(72) Inventors: Jerald Coleman Ensign, Madison, WI (US); Que Lan, Madison, WI (US); David Dyer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/279,119

(22) Filed: Sep. 28, 2016

(65) Prior Publication Data

US 2017/0334953 A1 Nov. 23, 2017

Related U.S. Application Data

(60) Continuation of application No. 14/216,468, filed on Mar. 17, 2014, now abandoned, which is a division of application No. 13/235,139, filed on Sep. 16, 2011, now abandoned.

(60) Provisional application No. 61/384,588, filed on Sep. 20, 2010.

(51) Int. Cl.
| | |
|---|---|
| *A61K 38/03* | (2006.01) |
| *C07K 14/24* | (2006.01) |
| *A01N 37/46* | (2006.01) |
| *A01N 63/02* | (2006.01) |
| *A61K 35/74* | (2015.01) |

(52) U.S. Cl.
CPC .............. *C07K 14/24* (2013.01); *A01N 37/46* (2013.01); *A01N 63/02* (2013.01); *A61K 35/74* (2013.01); *A61K 38/03* (2013.01); *Y02A 50/473* (2018.01); *Y02A 50/481* (2018.01)

(58) Field of Classification Search
None
See application file for complete search history.

(56) References Cited

U.S. PATENT DOCUMENTS

| | | | |
|---|---|---|---|
| 4,672,130 A | 6/1987 | Rhodes et al. | |
| 5,554,533 A | 9/1996 | Bedding et al. | |
| 5,827,872 A | 10/1998 | Webster et al. | |
| 5,972,687 A | 10/1999 | Smigielski et al. | |
| 5,997,269 A | 12/1999 | Feitelson | |
| 6,048,838 A | 4/2000 | Ensign et al. | |
| 6,103,228 A | 8/2000 | Heins et al. | |
| 6,379,946 B1 | 4/2002 | Ensign et al. | |
| 6,841,165 B1 | 1/2005 | Jarrett et al. | |
| 6,926,889 B2 | 8/2005 | Husseneder et al. | |
| 7,071,386 B2 | 7/2006 | Bintrim et al. | |
| 7,214,525 B1 | 5/2007 | Jarrett et al. | |
| 7,214,766 B2 | 5/2007 | Everett et al. | |
| 7,285,632 B2 | 10/2007 | Apel-Birkhold et al. | |
| 7,319,142 B1 | 1/2008 | Goldman et al. | |
| 7,517,956 B2 | 4/2009 | Bintrim et al. | |
| 7,585,944 B2 | 9/2009 | Apel-Birkhold et al. | |
| 2002/0147148 A1 | 10/2002 | Ensign et al. | |
| 2004/0194164 A1 | 9/2004 | Bintrim et al. | |
| 2006/0021087 A1 | 1/2006 | Baum et al. | |
| 2006/0159697 A1 | 7/2006 | Leclerc et al. | |
| 2008/0058248 A1 | 3/2008 | Apel-Birkhold et al. | |
| 2008/0104731 A1 | 5/2008 | Sheets et al. | |
| 2009/0144854 A1 | 6/2009 | Soberon-Chavez et al. | |
| 2009/0203612 A1 | 8/2009 | Bintrim et al. | |
| 2010/0004177 A1 | 1/2010 | Apel-Birkhold et al. | |
| 2012/0088719 A1 | 4/2012 | Ensign et al. | |

FOREIGN PATENT DOCUMENTS

| | | |
|---|---|---|
| WO | WO 1995/00647 | 1/1995 |
| WO | WO 1997/017432 | 5/1997 |
| WO | WO 1998/08388 | 3/1998 |

OTHER PUBLICATIONS

Encyclopedia Britannica (retrieved from https://www.britannica.com/topic/list-of-insects-2073946 on Jan. 29, 2018, 20 pages) (Year: 2018).*
Addullah et al. (2003) "Introduction of *Culex* Toxicity into *Bacillus thuringiensis* Cry4Ba by Protein Engineering," Appl Environ Microbiol 69(9):5343-5353.
Aguillera et al. (1993) "Bacterial Symbionts of *Steinernema scapterisci*," J Invert Pathol 62:68-72.
Ahantarig et al. (2009) "PirAB Toxin from *Photorhabdus asymbiotica* as a Larvicide against Dengue Vectors," Appl and Environ Microbiol 75(13):4627-4629, available online May 8, 2009.
Balcerzak, M. (1991) "Comparative Studies on Parasitism Caused by Entomogenous Nematodes, *Steinernema feltiae* and *Heterorhabditis bacteriophora*. I. The Roles of the Nematode-Bacterial Complex, and of the Associated Bacteria Alone, in Pathogensis," Acta Parasitologica Polonica 36(4):175-181.
Bode, H. (2009) "Entomopathogenic Bacteria as a Source of Secondary Metabolites," Curr Op in Chem Biol 13:224-230, available online Apr. 1, 2009.

(Continued)

*Primary Examiner* — Karlheinz R. Skowronek
*Assistant Examiner* — Ronald T Niebauere
(74) *Attorney, Agent, or Firm* — Leydig, Voit & Mayer, Ltd.

(57) ABSTRACT

Provided is a bacterial strain which produces a family of mosquitocidal toxins, *Xenorhabdus* MT, on deposit with the American Type Culture Collection, PTA-6826, insecticidal compositions comprising the mosquitocidal toxin(s) produced by *Xenorhabdus* MT, a mosquitocidal toxin preparation prepared from spent culture medium, whole culture or cells or a mixture thereof, of *Xenorhabdus* MT and method of insect control, especially mosquito control. Also provided are microbial compounds (same as mosquitocidal toxins) compositions comprising them and use in formulating therapeutic and other antimicrobial compositions, and methods of use for inhibiting microbial growth and for treating infection.

28 Claims, 5 Drawing Sheets

(56) References Cited

OTHER PUBLICATIONS

Boszormenyi et al. (2009) "Isolation and Activity of *Xenorhabdus* Antimicrobial Compounds Against the Plant Pathogens *Erwinia amylovora* and *Phytophthora nicotianae*," J Appl Microbiology 107:746-759, epub Mar. 23, 2009.
Bonifassi et al. (1999), "Gnotobiological Study of Infective Juveniles and Symbionts of Steinernema scapterisci: A Model to Clarify the Concept of the Natural Occurrence of Monoxenic Associations in Entomopathogenic Nematodes," Journal of Invertebrate Pathology 74, 164-172.
Bowen et al. (1998) "Purification and Characterization of a High-Molecular-Weight Insecticidal Protein Complex Produced by the Entomopathogenic Bacterium *Photorhabdus luminescens*," Appl Environ Microbiol. 64(8):3029-3035.
Brown et al. (2004) "A Novel Secreted Protein Toxin from the Insect Pathogenic Bacterium *Xenorhabdus nematophila*," J. Biol. Chem. 279(15):14595-14601.
Chaston et al. (2011), "The entomopathogenic bacterial endosymbionts Xenorhabdus and Photorhabdus: convergent lifestyles from divergent genomes," Plos ONE 6(11): 1-13.
Chu-Kung et al. (2004) "Effect of Fatty Acid Conjugation on Antimicrobial Peptide Activity," Dept of Chem Engineering Univ of CA, 6 pp.
Couche et al. (1987) "Occurrence of Intracellular Inclusions and Plasmids in *Xenorhabdus* spp.," J Gen Microbiol 133:967-973.
Duchaud et al. (2003) "The Genome Sequence of the Entomopathogenic Bacterium *Photorhabdus luminescens*," Nature Biotech 21(11):1307-1313.
Emelianoff et al, (2007), "Effect of bacterial symbionts Xenorhabdus on mortality of infective juveniles of two *Steinernema* species," Parasitol Res., 100:657-659.
French-Constant et al. (2000) "A Genomic Sample Sequence of the Entomopathogenic Bacterium *Photorhabdus luminescens* W14: Potential Implications for Virulence," Appl and Environ Microbiol 66(8):3310-3329.
Forst et al. (1997), "*Xenorhabdus* and *Photorhabdus* SPP: Bugs That Kill Bugs", Annu. Rev. Microbiol. 1997. 51:47-72.
Fodor et al. (Jul. 2010) "Comparative Analysis of Antibacterial Activities of *Xenorhabdus* Species on Related and Non-Related Bacteria in vivo," J Microbiol and Antimicrob 2(4):36-46.
Gaudriault et al. (Jul. 2008) "Plastic Architecture of Bacterial Genome Revealed by Comparative Genomics of *Photorhabdus* variants," Genome Biol 9:R117, 15 pp.
Givaudan et al. (2000) "*flhDC*, the Flagellar Master Operon of *Xenorhabdus nematophilus*: Requirement for Motility, Lipolysis, Extracellular Hemolysis, and Full Virulence in Insects," J Bacteriol 182(1):107-115.
Givaudan et al. (1996), "Cloning and nucleotide sequence of a flagellin encoding genetic locus from Xenorhabdus nematophilus: phase variation leads to differential transcription of two flagellar genes (fliCD)," Gene 183 (1996) 243-253.
Goodrich-Blair et al. (2007) "Mutualism and Pathogenesis in *Xenorhabdus* and *Photorhabdus*: Two Roads to the Same Destination," Mol. Microbiol. 64(2):260-268.
Grewal et al, (1997), "Mechanisms of speci® city of association between the nematode Steinernema scapterisci and its symbiotic bacterium," Parasitology, 114, 483-488.
Gualtieri et al (Apr. 2009) "Identification of a New Antimicrobial Lysine-Rich Cyclolipopeptide Family from *Xenorhabdus nematophila*," J Antibiotics 62:295-302.
Han et al. (2000) "Pathogenicity, Development, and Reproduction of *Heterorhabditis bacteriophora* and *Steinernema carpocapsae* Under Axenic," J Invertebrate Pathology 75:55-58.
Hinchliffe et al. (Mar. 2010) "Insecticidal Toxins from the *Photorhabdus* and *Xenorhabdus* Bacteria," Open Toxinology Journal 3:101-118.
Jarosz et al. (1991) "Involvement of Larvicidal Toxins in Pathogenesis of Insect Parasitism with the Rhabditoid Nematodes, *Steinernema feltiae* and *Heterorhabditis bacteriophora*," Entomophaga 36(3):361-368.

Khandelwal et al. (2003) "Insecticidal Activity Associated with the Outer Membrane Vesicles of *Xenorhabdus nematophilus*," Appl Env Microbiol 69(4):2032-2037.
Khandelwal et al. (2004) "Insecticidal Pilin Subunit from the Insect Pathogen *Xenorhabdus nematophila*," J. Bacteriol. 186(19):6465-6476.
Kirst, H. (2010) "The Spinosyn Family of Insecticides: Realizing the Potential of Natural Products," J of Antibiotics 63:101-111, published online Feb. 12, 2010.
Koppenhofer (2007), "Chapter 7: Bacterial symbionts of Steinernema and Heterorhabditis-Xenorhabdus innexi" In: Khuong B Nguyen: Entomopathigenic nematodes: systematics, phylogeny and bacterial symbionts, vol. 5, pp. 754-755.
Lang et al. (2008) "Linear and Cyclic Peptides from the Entomopathogenic Bacterium *Xenorhabdus nematophilus*," J. Nat. Prod. 71:1074-1077.
Lengyel et al. (2005) "Validation of Publication of New Names and New Combinations Previously Effectively Published Outside the IJSEM," Int. J. Systematic Evolutionary Microbiol 55:1395-1397.
Lengyel et al. (2005) "Description of Four Novel Species of *Xenorhabdus*, family *Enterobacteriaceae*: *Xenorhabdus budapestensis* sp. nov., *Xenorhabdus ehlersii* sp. nov., *Xenorhabdus innexi* sp. nov., and *Xenorhabdus szentirmaii* sp. nov.," System Appl Microbiol 28:115-122.
Lengyel et al. (2006) "Erratum to Description of Four Novel Species of *Xenorhabdus*, family *Enterobacteriaceae*: *Xenorhabdus budapestensis* sp. nov., *Xenorhabdus ehlersii* sp. nov., *Xenorhabdus innexi* sp. nov., and *Xenorhabdus szentirmaii* sp. nov.," System Appl Microbiol 30(1):83.
Lengyel et al. (2007) "Chapter 7: Bacterial Symbionts of Steinernema and Heterorhabditis—*Xenorhabdus innexi*," In: Khuong B. Nguyen: *Entomopathigenic Nematodes: Systematics, Phyloaeny and Bacterial Symbionts*, Koppenhöfer H.S. 5:754-755.
Li et al. (1995) "Identification of Two Pigments and a Hydroxystilbene Antibiotic from *Photorhabdus luminescens*," Appl Environ Microbiology 61(12):4329-4333.
Fischer-Le Saux et al. (1998), "PCR-Ribotyping of Xenorhabdus and Photorhabdus Isolates from the Caribbean Region in Relation to the Taxonomy and Geographic Distribution of Their Nematode Hosts", Appl Environ Microbiol, p. 4246-4254.
Morgan et al (2001) "Sequence Analysis of Insecticidal Genes from *Xenorhabdus nematophilus* PMFI296," Appl Env Microbiol 67(5):2062-2069.
Müller et al. (2007) "Sequencing and Analysis of the Biosynthetic Gene Cluster of the Lipopeptide Antibiotic Friulimicin in *Actinoplanes friuliensis*," Antimicrob Agents and Chemotherapy 51(3):1028-1037.
Nollmann et al. (Apr. 2012) "Synthesis of Szentiamide, a Depsipeptide from Entomopathogenic *Xenorhabdus szentirmaii* with Activity Against *Plasmodium falciparum*," Beilstein Journal J. Org. Chem. 8:528-533.
Richards et al. (2008) "*Xenorhabdus nematophila IrhA* Is Necessary for Motility, Lipase Activity, Toxin Expression, and Virulence in *Manduca sexta* Insects," J Bacteriology 190(14):4870-4879.
Rotem et al. (2009) "Antimicrobial Peptide Mimics for Improved Therapeutic Properties," Biochimica et Biophysica Acta 1788(8):1582-1589, available online Nov. 5, 2008.
Sergeant et al. (2003) "Interactions of Insecticidal Toxin Gene Products from *Xenorhabdus nematophilus* PMFI296," Applied and Environ Microb 69(6):3344-3349.
Sergeant et al. (2006) "Identification, Typing, and Insecticidal Activity of *Xenorhabdus* Isolates from Entomopathogenic Nematodes in United Kingdom Soil and Characterization of the *xpt* Toxin Loci," Applied and Environ Microb 72(9):5895-5907.
Sicard et al. (2004) "Stages of Infection During the Tripartite Interaction Between *Xenorhabdus nematophila*, Its Nematode Vector, and Insect Hosts," Appl Env Microbiol 70(11):6473-6480.
Sicard et al. (2004), "When mutualists are pathogens: an experimental study of the symbioses between Steinernema (entomopathogenic nematodes) and Xenorhabdus (bacteria)," J . Evol. Biol. 17: 985-993.

(56) References Cited

OTHER PUBLICATIONS

Sicard et al. (2005), "Specialization of the entomopathogenic nematode Steinernema scapterisci with its mutualistic Xenorhabdus symbiont," Naturwissenschaften, 92: 472-476.

Sugar et al. (2012), "Phenotypic variation and host interactions of Xenorhabdus bovienii SS-2004, the entomopathogenic symbiont of Steinernema jollieti nematodes," Environ. Microbiol.,14(4), 924-939, e-published Dec. 2011.

Tailliez et al. (2006) "New Insight Into Diversity in the Genus *Xenorhabdus*, Including the Description of Ten Novel Species," J Syst Evol Microb 56(12):2805-2818.

Talliez et al. (Aug. 2010), Phylogeny of Photorhabdus and Xenorhabdus based on universally conserved protein coding sequences and implications for the taxonomy of these two genera. Proposal of new taxa: *X. vietnamensis* sp. nov., *P. luminescens* subsp. *caribbeanensis* subsp. nov., *P. luminescens* subsp. *hainanensis* subsp. nov., *P. temperata* subsp. *Khanii* subsp. nov., *P. temperata* subsp. *Tasmaniensis* subsp. nov., and the reclassification of *P. luminescens* subsp. thracensis as *P. temperate* subsp. thracensis comb. nov., International Journal of Systematic and Evolutionary Microbiology, 60, 1921-1937.

Vigneux et al. (2007) "The *xaxAB* Genes Encoding a New Apoptotic Toxin from the Insect Pathogen *Xenorhabdus nematophila* Are Present in Plant and Human Pathogens," J Biol Chem 282(13):9571-9580.

Volgyi et al. (1998), "Phase Variation in Xenorhabdus nematophilus," Appl. Environ. Microbiol., 64(4), p. 1188-1193.

Waterfield et al (2005) "The *Photorhabdus* Pir Toxins Are Similar to a Developmentally Regulated Insect Protein but Show No Juvenile Hormone Esterase Activity," FEMS Microbiol Lett 245:47-52.

Waterfield et al. (2008) "Rapid Virulence Annotation (RVA): Identification of Virulence Factors Using a Bacterial Genome Library and Multiple Invertebrate Hosts," PNAS 105(41):15967-15972.

Waterfield et al. (Jun. 2009) "Photorhabdus and a Host of Hosts," Ann Rev Microbiol. 63:557-574.

Reimer, D (2013) Identification and characterization of selected secondary metabolite biosynthetic pathways from Xoneorhabdus nematophila, Doctoral Dissertation, Johann Wolfgang Goethe-Universitat, Frankfurt am Main (DE), 240 total pages.

Chemistry explained (retrieved from http://www.chemistryexplained.com/Pl-Pr/Primary-Structure.html on Aug. 20, 2015, 3 pages).

Search Report and Written Opinion, dated Dec. 6, 2011, corresponding to International Application No. PCT/US2011/052009 (filed Sep. 16, 2011), a corresponding application, 16 pp.

Patent Examination Report dated Jan. 21, 2014, for corresponding Australian Patent Application No. 2011305775.

Examination Report dated Feb. 14, 2014, for corresponding European Patent Application No. 11 761 230.9.

Examination Report dated Mar. 17, 2015, for corresponding European Patent Application No. 11 761 230.9.

\* cited by examiner

Figure 2

MOSQUITOCIDAL XENORHABDUS, LIPOPEPTIDE AND METHODS

CROSS-REFERENCE TO RELATED APPLICATIONS

This application is a continuation of U.S. application Ser. No. 14/216,468, filed Mar. 17, 2014, which in turn is a divisional of U.S. application Ser. No. 13/235,139, filed Sep. 16, 2011, which in turn claims the benefit of and priority to U.S. Provisional Application No. 61/384,588, filed Sep. 20, 2010. Each of these applications is incorporated by reference in its entirety herein.

BACKGROUND

The disclosure invention relates to insecticidal toxins produced by or isolated from bacteria, especially *Xenorhabdus*, and methods for the use of toxin-containing compositions or isolated toxins as insecticides and/or as insect control agents, and which exhibit antimicrobial activity, as well.

Biological agents are an important option for management of insect pests. One method of insect control explored was the use of certain genera of nematodes. Nematodes, including the *Steinernema* and Heterorhabditis genera, might be useful as biological agents, in part because of their transmissible insecticidal bacterial symbionts of the genera *Xenorhabdus* and *Photorhabdus*. Upon entry into the insect, the nematodes release their bacterial symbionts into the insect hemolymph where the bacteria reproduce and eventually cause insect death. The nematode then develops and reproduces within the insect cadaver. Bacteria-containing nematode progeny exit the insect cadaver as infective juveniles, which can then invade additional larvae to repeat the cycle of insect death and nematode propagation. While this cycle is easily performed on a micro scale in a laboratory setting, adaptation to the macro level, as needed to be effective as a general use insecticide, is difficult, expensive, and inefficient.

There are now also pesticide control agents commercially available that are naturally derived. These naturally derived approaches can be as effective as synthetic chemical approaches. One such naturally occurring agent is the crystal protein toxin produced by *Bacillus thuringiensis* (Bt). These Bt protein toxins have been formulated as sprayable insect control agents. Another application of Bt technology is the genetic modification of plants to contain and express the genes that encode the Bt toxins for protection from plant pests. Another microbial insecticide is the spinosyn complex of polyketide molecules produced by the bacterium *Saccharopolyspora spinosa*. Spinosyn has been formulated as a spray for insect pests including house flies and mosquitoes. See, e.g., Kirst, H. A. (2010) J. Antibiotics 63:101-111; Sheehan et al. (2006) J. Nat. Prod. 69:1702-1710.

The genus *Xenorhabdus* is a member of the family Enterobacteriaceae; *Xenorhabdus* occurs in nature in a symbiotic association with the entomopathogenic nematode *Steinernema*. The nematode is the vector for transmission of the bacteria between insects. The bacteria produce a complex of protein toxins that kill the insect victim. The nematode reproduces in the insect cadaver ultimately differentiating to an infective juvenile stage, each carrying *Xenorhabdus* cells in its intestine. Another related bacterium, *Photorhabdus*, is similarly associated with the nematode Heterorhabditis (Mol. Microbiol. 64: 260. 2007. Ann Rev Microbiol. 63; 557. 2009).

*Xenorhabdus* and *Photorhabdus* both produce antibiotic molecules that are thought to maintain the insect cadaver as an efficient growth chamber for their respective nematode associates (Current Opinions Chemical Biol. 13: 224. 2009. Appl. Environ. Microbiol. 61:4329. 1995), and both produce toxins that are toxic when injected or fed to insects. This was first discovered for *Photorhabdus* by Bowen and Ensign (Appl Environ Microbiol. 64: 3029. 1998). A complex of four proteins varying from 30 to 200 kDa, named the tc complex, was shown to be toxic when fed to a wide variety of insect pests including mosquito larvae (WO97/17432. 1997).

Subsequently, a variety of insecticidal proteins produced by one *Xenorhabdus* species, *X. nematophila*, were described. Morgan et al (Appl. Env. Microbiol. 67, 2062. 2001) isolated several species of *X. nematophila* that produced a 280 kDa protein complex that was orally active against *Pieris brassiceae* (cabbage moth) larvae. Brown et al (J. Biol. Chem. 279:14595. 2004) reported a 42 kDa toxin lethal when injected into two species of insect larvae. Ribeiro et al described a 10,790 Da protein that lyses insect hemocyte cells and mammalian red blood cells, however activity against insects was not reported. Vigneux et al (J. Biol. Chem. 282: 9571. 2007) reported similar cell damaging activity caused by a 78 kDa protein produced by the same species of bacteria, but again insect toxicity was not reported. Khandelwal et al (Appl. Env. Microbiol. 69: 2032. 2003) reported the insecticidal activity of a large molecular complex of proteins associated with outer membrane vesicles of *X. nematophilus* and later these authors reported a 17 kDa protein isolated from the complex that is orally toxic to *Helicoverpa armigera* larvae and cytotoxic to hemocytes of the insect (J. Bacteriol. 2004:6465. 2004). Lang et al (J. Nat. Prod. 71: 1074. 2008) isolated three low molecular weight peptides from *X. nematophila* that are insecticidal, and one of the peptides, 662 Da in size, showed weak insecticidal activity against one insect and against a crustacean (brine shrimp, Artemia). A family of five lysine rich cyclopeptide antibiotics, none with insecticidal activity, was described by Gualtieri et al (J. Antibiotics 62:295, 2009). Significantly, there are limited reports of mosquitocidal toxins produced by *Xenorhabdus* bacteria. U.S. Pat. Nos. 6,048,838 and 6,379,946 report mosquitocidal activity for proteins produced by twelve natural isolates of *Xenorhabdus*.

The sequenced genome of *Photorhabdus luminescens* tto1 revealed two genes coding for proteins which, when produced in recombinant *Escherichia coli*, were toxic to larvae of three mosquito species (Duchaud et al Nature Biotech 21:1307. 2003). The gene products were shown to be proteins of 45 and 14 Da (Waterfield et al FEMS Microbiol Lett 245:47. 2005). The same toxin, named PirAB, produced by another *Photorhabdus* species, *P. asymbiotica*, was lethal to *Aedes aegypti* and *A. albopictus* mosquitoes (Appl. Env. Microbiol 75: 4627. 2009). US WO 97/17432 (Ensign et al.) reported mosquitocidal activity for the tca complex of insecticidal proteins produced by *P. luminescens* strain W14. The toxin XLT described in the present application is believed to be the first low molecular weight mosquitocidal lipopeptide of either *Xenorhabdus* or *Photorhabdus*.

Bacteria of the genus *Xenorhabdus* are symbiotically associated with the *Steinernema* nematode. These bacteria only had pesticidal activity when injected into insect larvae and did not exhibit biological activity when delivered orally (see Jarosz J. et al. Entomophaga 36 (3) 1991 361-368; Balcerzak, Malgorzata. Acta Parasitologica Polonica, 1991, 36(4), 175-181).

There are *Xenorhabdus* toxins which are produced and secreted by growing bacterial cells of the genus *Xenorhabdus*. The protein complexes, with a native molecular size ranging from about 800 to 3000 Da, can be separated by SDS-PAGE gel analysis into numerous component proteins. The toxins exhibit significant toxicity upon exposure to a number of insects. Furthermore, toxin activity can be modified by altering media conditions. In addition, the toxins have characteristics of being proteinaceous, with activity that is heat labile and sensitive to proteolysis. See U.S. Pat. No. 6,048,838, for example.

Because mosquitoes are a common insect pest and are also important as vectors of serious human disease, it is important to find environmentally friendly, economical and effective means for their control.

It has been difficult to effectively exploit the insecticidal properties of the nematode or its bacterial symbiont. Thus, it would be quite desirable to discover insecticidal agents derived from *Xenorhabdus* bacteria that have oral activity so that the products produced therefrom could either be formulated as a sprayable insecticide or the bacterial genes encoding said proteinaceous agents could be isolated and used in the production of transgenic plants.

There is a need in the art for environmentally friendly, economical and effective means of insect control, especially mosquito control for benefits in human and animal health and the comfort of both humans and animals.

BRIEF SUMMARY

Provided is an easily administered mosquitocidal lipopeptide toxin (XLT), as a purified peptide, contained within bacterial cells, in stationary phase cultures, in spent culture medium or in concentrated spent culture medium, dried spent culture medium, dried whole culture material, or dried or concentrated late log or stationary phase culture medium (including cells). Dried material can be in powder or pellet form, or in slow release solids. Optionally, crude preparations, cultures, culture supernatants, or cells are heat-treated prior to formulation as mosquito control compositions. Specifically, this mosquitocidal toxin is produced by *Xenorhabdus innexi* strain *scapterisci*, also called *Xenorhabdus* MT herein, and deposited as PTA-6826 with the American Type Culture Collection, PO Box 1549, Manassas, Va. 20108 on Jul. 1, 2005. All restrictions upon access to the strain will be irrevocably released upon grant of a patent based on the present application, and if necessary, the deposited strain will be replaced for thirty years from the date of deposit or five years after the last request for same.

The mosquitocidal lipopeptide toxin described herein can be comprised within compositions which further contain one or more additional insecticidal agents, chemical or biological. Biological insecticidal agents can be specific for mosquitoes or they can be specific to one or more insects of choice. Examples of biological insecticidal agents include insect viruses (for example a baculovirus specific for a target insect of choice, i.e., mosquito or other insect; a bacterial insecticidal toxin specific for mosquitoes and/or other insects; a bacterial insecticidal toxin such as one or more produced by a *Bacillus sphaericus* or a *Bacillus thuringiensis israeliensis* strain, a *Xenorhabdus* or a *Photorhabdus* strain, one or more spinosyn compounds or a plant derived insecticidal toxin such as an insect specific plant defensin.

Also provided is a method for delivering insecticidal toxins that are functionally active and effective against various insects, including Dipteran insects, for example, those of *Culicidae, Aedes, Culex, Ochlerotatus* and *Armigeres*, with the method comprising the step of applying to an environment in which mosquitoes reproduce a composition containing live or dead cells of *Xenorhabdus* MT, culture medium (with or without cells) in which the strain has been grown, dried culture medium, concentrated culture medium or the like, in an amount effective to control mosquito reproduction.

The mosquitocidal composition can be applied to mosquito- or other sensitive insect-infested environments such as stagnant water, puddles, or vegetated areas such as lawns, golf courses, parks and the like. Whole culture broth, cell free spent medium, or dried or concentrates of either of the foregoing or dried compositions, including dried powders or suspended aerosols of dried material, can be applied in such environments to achieve control of mosquitoes or other sensitive insects, and the reproduction of those mosquitoes and sensitive insects. Optionally, such materials are heat-treated, for example, at 100° C. for 10 min prior to formulation. Advantageously, the mosquitocidal compositions result in ingestion of the toxin by insects, especially larvae, in amounts sufficient to kill or at least reduce reproduction of those insects. In an embodiment, the mosquitocidal toxin is formulated in a bait to trigger ingestion by the insect or its larvae.

Also encompassed by the use of the XLT described herein for control of mosquito populations are methods for controlling mosquito-borne diseases including, but not limited to, lymphatic filariasis, West Nile Fever, chikungunya fever, malaria, dengue fever, certain viral encephalitis diseases and yellow fever.

Further provided herein are XLT lipopeptides and compositions comprising them useful as antimicrobial agents and related methods for inhibition of microbial growth using the XLT(s) of the present invention. These materials disclosed herein have potent antimicrobial activities and are useful against Gram positive and Gram negative bacteria including, but not limited to, *Escherichia coli, Salmonella enteriditis, Salmonella typhimurium, Salmonella agona, Listeria monocytogenes, Staphylococcus aureus, Pseudomonas aeruginosa, Micrococcus luteus, Bacillus cereus*, and fungi including, but not limited to, *Candida albicans*. These compounds are effective for use in human and/or veterinary medicine, or as agents in agricultural, food science or industrial applications. Antimicrobial compounds of the present invention are also useful for inhibiting the microbial growth and for treating infections in humans or animals caused by those pathogens listed above and other microorganisms as well.

In an embodiment, an antimicrobial peptide is integrated in a larger peptide or protein. In an embodiment, a peptide of the invention is covalently or non-covalently associated with another compound, for example, a polymer.

The antimicrobial XLT lipopeptides described herein are useful as bactericides and/or bacteriostats for modification of infectivity, killing microorganisms, or inhibiting microbial growth or function and thus useful for the treatment of an infection or contamination caused by such microorganisms.

Also provided are therapeutic or otherwise active compositions suitable for human, veterinary, agricultural or pharmaceutical use, comprising one or more of the antimicrobial peptides of the invention and a suitable pharmaceutical carrier. Such therapeutic compositions can be formulated and administered as known in the art, e.g., for oral, mucosal, inhalation, parenteral or topical application for controlling and/or preventing infection by a wide range of microorganisms including gram-positive and gram-negative bacteria.

Pharmaceutical compositions contain a therapeutically effective amount of one or more of the antimicrobial lipopeptides and a suitable carrier. The carrier is chosen according to the intended use and route of administration. A therapeutically effective amount of an antimicrobial lipopeptide can be readily determined according to methods well known in the art. For example, the amount will vary depending on the severity of an infection, concomitant therapy, subject parameters such as the age and the size/weight of a subject with an actual or potential infection of a given microorganism, and the route of administration and the like.

The present disclosure relates to compositions comprising one or more antimicrobial lipopeptides disclosed herein in a microbicidally effective amount and a pharmaceutically acceptable carrier. Such compositions may additionally comprise a detergent. The addition of a detergent to such peptide compositions is useful to enhance antibacterial characteristics of the peptides, or an additional antimicrobial agent such as triclosan, or an antibiotic, including but not limited to, bacitracin, neomycin, tetracycline, azithromycin, gentamycin, doxycycline, erythromycin, penicillin, ampicillin, cephalosporin, or a quinolone or fluoroquinoline antibiotic. Although any suitable detergent may be used, an exemplary detergent is a nonionic detergent such as Tween™ 20 or 1% NP40. Such antimicrobial pharmaceutical compositions can be formulated and administered in ways, as understood in the art for use local or systemic injection, for oral or topical application. In an embodiment, the antimicrobial peptides of the present invention can comprise from 0.0001% to 50% by weight of such compositions.

It will be understood that a composition for application, e.g. by systemic injection, contains an antimicrobial peptide in a therapeutically effective amount or a therapeutically effective amount of an antimicrobial XLT lipopeptide can be conjugated to another molecule with specificity for the target cell type. The other molecule can be an antibody, ligand, receptor, or other recognition molecule. In an embodiment, the choice of the lipopeptide or lipopeptides is made with consideration of immunogenicity and toxicity for an actually or potentially infected host, effective dose of the peptide, and the sensitivity of the target microbe to the peptide, as known in the art. In another embodiment the antimicrobial XLT lipopeptide(s) can be incorporated in a therapeutically effective amount into a composition for topical application, such as an ointment, gel, salve, lotion or other form, in which instance, potentially toxic activity is less important than for internal or oral administration.

In an embodiment, the method of inhibiting the growth of bacteria using the XLT lipopeptides disclosed herein may further include the addition of one or more other antimicrobial agents (e.g. a conventional antibiotic) for combination or synergistic therapy. The appropriate amount of the peptide administered will typically depend on the susceptibility of a bacterium such as whether the bacterium is Gram-negative or Gram-positive or the susceptibility of a fungus, for example, Candida albicans, and is easily discerned by one of ordinary skill in the art.

In an embodiment there is a composition that comprises one or more XLT lipopeptides, in an amount effective to kill a microorganism, and a suitable carrier. Such compositions may be used in numerous ways to combat microorganisms, for example in household or laboratory antimicrobial formulations using carriers well known in the art.

Objects, advantages, and features of the present disclosure will become apparent from the present specification.

BRIEF DESCRIPTION OF THE DRAWINGS

FIG. 2 shows the response of *A. aegyptii* larvae to the *Xenorhabdus* mosquitocidal toxin.

FIG. 5A shows retention time (0-70 min) versus absorbance units. FIG. 5B is an expanded view of the 40-65 minutes, with peak mosquitocidal activity marked with arrows, and estimated molecular weights indicated.

DETAILED DESCRIPTION

Figure 1:
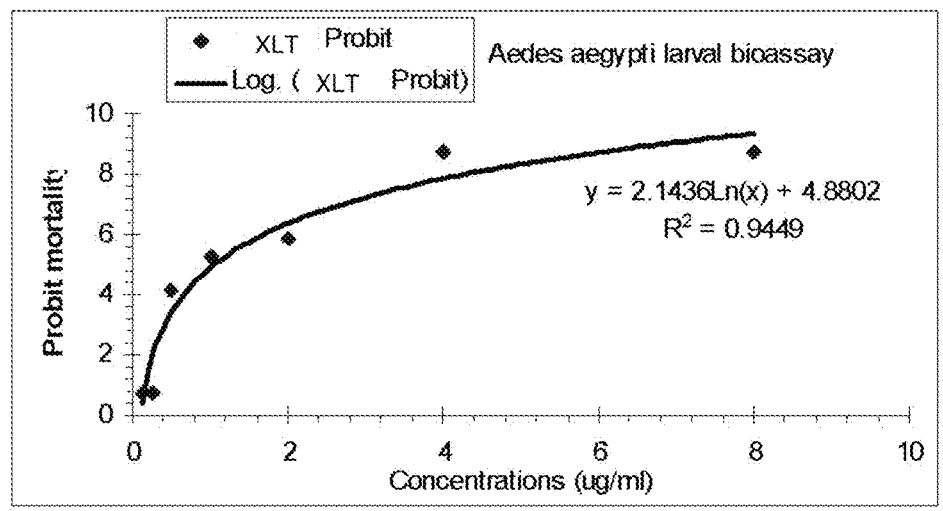
FIG. 1 is a dose response curve for exposure of *A. aegyptii* larvae to the *Xenorhabdus* mosquitocidal toxin.

A strain of *Xenorhabdus* (identified as X. innexi herein) called MT herein, was isolated from an entomopathic *Steinernema scapterisci* nematode. This species is found only in the intestinal tract of certain infective juvenile stage nematodes, for example from the genus *Steinernema* (Lengyel et al. (2005) System. Appl. Microbiol. 28:115-122 reported isolation of *Xenorhabdus innexi* from *S. scapterisci* nematodes; this strain did not appear to exhibit mosquitocidal activity.

The *Xenorhabdus innexi* strain MT described herein was deposited with the American Type Culture Collection (ATCC), 10801 University Boulevard, Manassas, Va. 20110-2700 on Jul. 5, 2005, in accordance with the provisions of the Budapest Treaty, and this strain has been assigned identification number PTA-6826: This strain deposit will be maintained without restriction in the ATCC depository for a period of 30 years, or 5 years after the last request, or for the effective life of the patent, whichever is longer, and will be replaced if the deposit becomes nonviable during that period. Upon grant of a patent, all restrictions imposed by the depositor on the availability to the public of the deposited biological material will be irrevocably removed.

This bacterium was found to produce a low molecular weight lipopeptide (or family of lipopeptides) that is (are) a potent toxin of mosquito larvae, which has been purified. MALDI-TOF mass spectrophotometric analyses revealed the molecular weights of the toxic lipopeptide varied from about 1182 to about 1431 daltons. Without wishing to be bound by theory, it is believed that the variation in molecular weight is due to variability in the fatty acid moieties covalently liked to the peptide. The N-terminal sequence of the peptide portion of the toxin as determined by amino acid analyses was searched in available databases, but no matches were obtained. Amino acids in the XLT lipopeptide are believed to include diamobutyric acid, histidine, aspartate, asparagine, glycine and serine. While the specifically exemplified fatty acids are shown, it is understood that other fatty acids can be covalently linked to the peptide without loss of insecticidal activity; Other fatty acid moieties can be those n-saturated fatty acids of C8 to C20, or C10 to C18, as well as 2-oxo-fatty acids of C8 to C20 or C10 to C18, monounsaturated fatty acids of C8 to C20 or C10 to C18, among others, provided that mosquitocidal activity is maintained. The fatty acyl moiety can be from 8-20 carbons, and is a straight chain fatty acyl, a 2-, 3-, 4-, 5-, 6-, 7-, 8-, 9-, 10-, 11-, 12-13-, 14-, 15-, 16-, 17-, 18-, 19- or 20-oxo-fatty acyl, a 3-oxo-fatty acyl or a 4-oxo-fatty acyl moiety.

The mosquitocidal activity is both secreted from cells into growth media and retained by the cells, especially on the cell surface. The activity is stable with no loss of activity of crude or purified material during two years incubation at room temperature. The activity is not inactivated by heat or by 0.1 N HCl or 0.1 N NaOH, with treatment for 24 hr. A dried powder of culture broth with cells retained activity for more than two years. The active component is also relatively stable to heat, ultraviolet light irradiation, freezing, drying, protease digestion and certain other conditions.

The mosquitocidal activity of this toxin is potent: 1-10 nanograms in a 1 mL culture killed all 20 larvae challenged, i.e. it is 100% lethal to mosquito larvae in 24 hours; put another way, 10 ng is the minimum lethal dose for 3-5 instar *A. aegypti* larvae. Purified preparations can cause larval death in 2-3 hours. It is equally active against larvae of *Anopheles, Aedes* and *Culex* mosquitoes. By contrast, this *Xenorhabdus* MT mosquito toxin is not (or is minimally) toxic to wax moth larvae, tobacco horn worm larvae, Colorado potato beetle larvae and fruit fly larvae upon ingestion. Thus, it appears that this *Xenorhabdus* toxin does not have broad spectrum insecticidal activity. In addition, this XLT is not active against Artemia (brine shrimp) larvae, the nematode *Caenorhabditis elegans*, or cultured *Manduca sexta* cells, nor does it cause hemolysis of human or animal (rabbit, sheep) red blood cells or damage to mammalian cells, as specifically exemplified by cultured bovine kidney epithelial cells or mouse macrophages.

This highly stable toxin can be formulated as a spray or a finely divided, dry material to be administered in areas where mosquitoes reproduce and in bait compositions for widespread control of mosquito pests. Mosquito-borne diseases are becoming an increasingly worldwide problem. Current usable strategies employ chemical and microbial agents to kill mosquito larvae. However, mosquito vectors of malaria, dengue fever, yellow fever and viral encephalitis are becoming resistant to these agents following their widespread and long term use. This *Xenorhabdus* XLT toxin is believed to be unique among bacteria-derived agents in being active against the three major genera of problematic mosquitoes and in being highly stable and resistant to desiccation and heat. Because it is stable to drying and heat, this toxin can be produced, stored and distributed cheaply. It is possible to use dried culture medium or dried cell preparations directly with little or no purification.

The XLT toxin described herein has significant advantages over two currently employed biological mosquito control agents, *Bacillus thuringiensis* israeliensis and *Bacillus sphaericus*. The toxins produced by these bacteria are large protein molecules inactivated by UV light, heat and proteases, and they settle rapidly in aquatic environments. Consequently they must be applied in multiple doses, which is both expensive and increases the potential for development of resistant mosquitoes. Resistance of mosquitoes to these bacterial toxins has increased in recent years a consequence of long term application in the field, and there is concern that these agents might become obsolete in the near future (Science 200: 328. 2003). In addition, neither of these toxins is lethal to all species of disease carrying mosquitoes.

Another significant advantage of XLT is low cost of production, XLT is produced in an inexpensive mineral salts medium with glucose or glycerol with vitamin supplements, and the entire culture can be drum-dried at high temperature to a stable preparation easy to apply in the field by conventional means. Mosquitoes are the most medically important arthropod transmitted agents of infectious disease causing dengue fever, West Nile fever, chikungunya fever, yellow fever, malaria, lymphatic filariasis and many viral diseases. The economic impact of these diseases, especially in developing countries, is staggering. Malaria is estimated to affect 500 million people, causing 3 million deaths annually and is estimated to kill one child in Africa every 30 seconds (National Geographic, July 2007). With the possibility of global warming, the geological distribution of mosquitoes is expected to expand, accompanied by increased incidence of diseases that they transmit. The *Xenorhabdus* lipopeptide toxin, XLT, is an important addition to the mosquito control arsenal and aids in limiting the extent of the diseases they transmit.

The present mosquitocidal material can be combined with other insecticidal agents, including *Bacillus thuringiensis, Bacillus sphaerius*, spinosyn (polyketide insecticides produced synthetically or by *Saccharopolyspora* or other insecticidal material.

The mosquitocidal toxin activity is found in culture broth and is associated with cells, with maximum levels obtained at the late logarithmic phase of growth, at about 2-3 days of incubation at temperatures 28-33° C. Less mosquitocidal toxin is produced at 20° C., and this bacterium does not grow at 37° C. The mosquitocidal toxin is also associated with the surface of the bacterial cells. Optimum media for production of this toxin include both complex growth media (nutrient broth) and defined mineral salts medium with glucose or glycerol as carbon source.

The active molecule was purified from culture broth by acetone precipitation, ion exchange chromatography and high pressure liquid chromatography (HPLC). The toxin is a lipopeptide molecule varying in size from about 1182 to about 1431 daltons. The peptide component contains eight amino acid residues: 2 histidine, 2,3-diaminobutyrate, 3 asparagine (and/or aspartic acid), glycine and serine. The fatty acid component is primarily 2-oxodecanoic acid (C10) and 2-oxo-dodecanoic acid (C12), but other longer chain fatty acids appear to be present in toxin preparations as well, thus accounting for the variable molecular weights. Each of the variable sized molecules (separate HPLC peak fractions) has mosquitocidal activity.

The toxin is not inactivated by desiccation, freezing, ultraviolet light irradiation, by heating to 120° C. for 30 min, or incubation in 0.1 N NaOH or 0.1 N HCl, and it is not inactivated by treatment with any protease tested to date. Samples of cultures dried at 60° C. retained full activity after storage for more than three years at room temperature.

The stability to UV light, heat, proteases and desiccation are significant advantages over currently used biological mosquito control agents. Production of the toxic activity in inexpensive and defined growth media will be of economic significance. The toxins of *Bacillus thuringiensis* israeliensis and *Bacillus sphaericus*, two biological agents marketed for mosquito control, are large proteins that are inactivated by heat, UV light and proteases; therefore they must be applied in multiple doses. Moreover, in recent years, mosquitoes have developed resistance to these toxins, and there is thus concern that these agents may become obsolete in the near future. Spinosyn, a 21 carbon tetracyclic lactone with two sugar moieties, is also marketed for mosquito control.

In a pilot experiment, a dried *Xenorhabdus* MT culture preparation was added to stagnant water from a forested swamp (100 mg dried culture powder per 100 mL), and containers were placed in a forest swamp area during the summer. Pots containing stagnant water plus dried *Xenorhabdus* MT culture contained no mosquito larvae after two weeks, while control pots of stagnant water only contained 20-85 live mosquito larvae after the same period of time. This supports that the preparations described herein are useful in insect control in the field.

As used herein, a "pure culture" of a bacterium means that there are no other strains or other species of bacteria present. In certain contexts, there are not more than 1 cell of other strains or species in $10^7$ cells in the culture.

An isolated or purified XLT, as used herein, refers to "isolated" to this molecule when it is not associated with the other molecules with which it would be found in nature. Thus, reference to "isolated" and/or "purified" signifies the involvement of the "hand of man" as described herein.

By toxin activity against an insect it is meant that a protein functions as an orally active insect control agent (alone or in combination with other proteins), as demonstrated by its ability to disrupt or deter insect activity, growth, and/or feeding. Toxin activity may or may not cause death of the insect. When an insect comes into contact with an effective amount of a "toxin" of the subject invention delivered via formulated protein composition(s), sprayable protein composition (s), a bait matrix or other delivery system, the results are typically death of the insect, inhibition of the growth and/or proliferation of the insect, and/or prevention of the insects from feeding upon the source that makes the toxin available to the insects.

In the present context, a mosquitocidal toxin is a protein which functions as an orally active mosquito control agent (alone or in combination with other proteins), as demonstrated by its ability to disrupt or deter insect activity, growth, and/or feeding. Toxin activity may or may not cause death of the mosquito, but advantageously causes death. When a mosquito ingests an effective amount of a "toxin" of the subject invention delivered via formulated protein composition(s), sprayable protein composition (s), a bait matrix or other delivery system, the results are typically death of the mosquito, inhibition of the growth and/or proliferation of the mosquito.

As used herein, insecticidal activity, as related to the XLT described herein, refers to the capacity of the XLT toxin to kill, inhibit growth and/or reproduction or otherwise negatively affect all or part of an insect pest, especially an adult or juvenile mosquito or related insect, especially upon oral ingestion of the XLT toxin. Complete lethality to feeding insects is preferred but is not required to achieve functional activity. If an insect avoids the toxin or ceases feeding, that avoidance will be useful in some applications, even if the effects are sublethal or lethality is delayed or indirect. It is understood that the XLT toxin may be truncated and still retain functional activity. As used herein, the term "toxin" is also meant to include functionally active truncations, and truncation can include less than all the specifically exemplified and/or less than the full fatty acylation as disclosed herein.

In addition, there can be amino acid substitution in the XLT, provided that insecticidal and/or insect toxic activity is retained. Advantageously, the amino acid substitutions are conservative, that is, amino acids of similar physical properties for those substituted for (basic amino acid for basic amino acid: lysine for diaminobutyric acid and histidine; glutamine for asparagine; threonine for serine, serine for cysteine, cysteine for serine, or alanine for glycine, for example.

An amount of the XLT effective for insect control, as used herein, refers to an amount of the toxin which is sufficient to cause at least significant growth inhibition, developmental retarding or inhibition of fertility or death of at least one developmental stage of the insect, especially a larval stage, of an insect which is advantageously but not only a Dipteran insect including but not limited to a mosquito.

Target insects, especially but not only mosquito larvae as well as adults, are contacted with the XLT and allowed to ingest it so that insect control results. Advantageously, the XLT is formulated for ease of application to an environment in which the insect occurs and reproduces. The toxin can be in the form of a whole culture concentrate, a dried whole culture concentrate or dried preparation of a whole culture concentrate, cells or culture supernatant. A dried formulation can include bait which would attract insects including mosquitoes and induce ingestion of the toxin-containing material so as to result in insect control.

The XLT lipopeptides disclosed herein also have potent antimicrobial activity against a wide range of microorganisms including gram-positive and gram-negative bacteria and fungi. Detailed description of the microorganisms belonging to gram-positive and gram-negative bacteria can be found in Medical Microbiology (1991), 3rd edition, edited by Samuel Baron, Churchill Livingstone, N.Y. Examples of susceptible bacteria include, but are not limited to, *Escherichia coli, Salmonella typhimurium, Pseudomonas aeruginosa, Staphylococcus aureus, Staphylococcus epidermidis* and *Bacillus cereus*. It is understood that additional gram-positive and gram-negative bacteria are sensitive, and it is further appreciated that the in vitro tests described herein model the effects of the present antimicrobial peptides in topical, local, respiratory or systemic use in a human or animal. In vitro antimicrobial activity of these peptides, as demonstrated herein, is an accurate predictor of in vivo antimicrobial activity.

Isolation and Characterization of *Xenorhabdus* MT

A collection of 143 *Xenorhabdus* strains that had been isolated from nature by an insect baiting technique were tested for their ability to kill mosquito larvae. Each isolate was grown in a complex nutrient broth medium for 3 days and 50 and 100 µl samples of the cultures were tested using 3-4 instar larvae of *Aedes aegypti*. 15-20 larvae were placed in 0.5 mL water in chamber wells of a 24 well tissue culture dish. Observations using a dissecting microscope were made after 24 and 48 hours incubation at room temperature. Control and unaffected larvae remained actively motile. Larvae that became immobile were scored as killed. Approximately 80% of the isolates showed no mosquitocidal activity. Just one of those that showed activity killed all larvae within 24 hr, the other isolates were clearly less active. A 10 µl sample of the culture broth of this most active isolate killed all of the test larvae in 5-6 hours. This one mosquitocidally active bacterium was isolated from the infective juvenile stage nematode *Steinernema scapterisci*, which had been obtained from G. C. Smart Jr., University of Florida. It is well known that the *Steinernema* nematodes carry pure cultures of the *Xenorhabdus* in their intestines. However, the report from the Smart laboratory (Smart et al. 1993. J. Invert. Pathol. 62:68-72) described isolation of several bacteria other than *Xenorhabdus*. None of these appears to have been tested for insecticidal activity. Without wishing to be bound by any particular theory, it is believed that the surfaces of those nematodes were not completed sterilized because the results were inconsistent with other reports.

To avoid contamination with bacteria found on the surfaces of the nematodes, the nematodes were surface sterilized by incubating in 5% sodium hypochlorite (Chlorox™) for 3 minutes and then washing with sterile water. 25 of the nematodes were placed in the well of a sterile depression microscope slide and cut into small pieces using a sterile scalpel blade. A drop of this mixture was streaked onto the surface of a Petri dish containing nutrient agar. After 3 days incubation at 30° C. all the colonies of bacterial growth appeared to be of one type, 3-5 mm in diameter, tan and turbid. Each colony formed blue colonies on a nutrient agar medium containing tetrazolium and brom phenol blue dyes, which is a signature feature of Xenorhabdus bacteria. Microscopic examination of the bacteria in ten colonies revealed that each contained a single morphological shape, i.e., rod-shaped bacteria 2×5 um in size, with each cell containing intracellular inclusion proteins. These inclusion proteins are characteristic of Xenorhabdus and Photorhabdus bacteria. The bacterium was assigned the name Xenorhabdus innexi scapterisci, also called Xenorhabdus MT herein and on deposit as ATCC PTA-6826. Cultures of each of these colonies were equally effective in killing A. aegypti larvae. Subsequently, the same bacterium was isolated from Steinernema scapterisci nematodes obtained from R. Han in Guangzhou, China and from Becker Underwood Company in Ames, Iowa. Both of these isolates were equally toxic to mosquito larvae as the first isolate. Equivalent isolates can be isolated from *Steinernema scapterisci* nematodes.

Lengyel et al (Int. J. Systematic Evolutionary Microbiol. 55: 1395. 2000) reported the isolation of *Xenorhabdus* from *S. scapterisci* nematodes and assigned the genus and species name *Xenorhabdus innexi*. The isolate has been deposited in the German Culture Collection DSM. The culture was purchased from DSM and shown to be the similar to *Xenorhabdus* MT culture described herein above, based on 16S ribosomal RNA analysis and similar physiological properties. However, the DSM culture differed in that it was not mosquitocidal. The bacterium was reported in the Lengyel paper to form red colonies on the nutrient agar-dye medium. It is well known that *Photorhabdus* and *Xenorhabdus* undergo a phase variation process, whereby variant cells arise spontaneously in culture media. These variants, called secondary variants, lose many properties of the parent culture and form red instead of blue colonies on the dye medium. The DSM culture of *S. innexi* is thus a secondary variant. The bacterium herein is now assigned the name *Xenorhabdus* innexi strain *scapterisci*; this strain is deposited with the ATCC, as indicated above. A revertant of the DSM secondary variant was isolated by one of the present inventors. The revertant acquired the original phase properties of forming blue colonies on dye medium, exhibited mosquitocidal activity and in liquid culture produced peptides of a pattern similar (or identical) to that of *Xenorhabdus* MT.

Production and Purification of XLT

The optimum growth conditions for production of XLT were determined. The test culture growth media were inoculated with cells from a blue colony of *X. innexi scapterisci* grown on nutrient agar dye medium. 50 mL of test media in 500 mL Erlenmeyer flasks were shaken at 180 rpm at various temperatures. Samples of 5 mL each were removed at 24 hour intervals and centrifuged at 10,000 rpm for 15 min at room temperature to remove cells. A 10 μl sample of the supernatant fluid of each culture was tested for mosquitocidal activity. The results shown in Table 1 show that mosquitocidal activity appears in the complex growth medium nutrient broth at 2 days, reaches a maximum level at 3 days and remains constant for 14 days. The optimum temperature for toxin production is 30° C.; note that this bacterium did not grow at 37° C. Less activity was produced in two other complex media, Bacto peptone and Proteose peptone (Difco, Detroit, Mich.). Addition of glucose to nutrient broth did not increase XLT formation. The highest level of toxin production, lowest minimal lethal dose) is greatest in the mineral salts medium containing a vitamin mixture (for example, 1.0 mL per 100 mL defined medium of Sigma vitamin mixture (Sigma-Aldrich™, St. Louis, Mo.; catalog number v1-1 kt, complete vitamin mixture, or nicotinamide) or yeast extract and either glucose or glycerol as carbon and energy source. These results show that optimum conditions for toxin production are in cultures growing aerobically at 30° C. in the defined growth media after 3 days incubation. Cultures not centrifuged to remove cells are twice as toxic as the supernatant fluids not containing bacterial cells, the MLD for whole cultures of both nutrient broth and mineral salts is 2.5 μl. A 10 μg sample of a MS (minimal salts) glucose culture dried at 60° C. was lethal to all of the test mosquito larvae in less than 5 hours. Cells of the bacterium removed by centrifugation were found to be toxic to the mosquito larvae. It is estimated that about half the toxin is cell-associated and half is in the culture medium.

The location of the toxin in the cells was investigated. Table 2 shows that a dose of $5\times10^7$ of the cells was lethal to the larvae. Killing the bacterium by heating the cells to 90° C. for 20 minutes did not decrease the activity, showing that the toxicity is not due to bacterial infection of the larvae. Disruption of the cells, followed by centrifugation, reveals that all the toxin activity is associated with the cell surface (wall-membrane); no activity was present in the cell cytoplasm. A small amount of activity was removed from the cells by incubation with salt, more was released by dilute acid and nearly all activity was removed by dilute alkali.

XLT was found to be toxic to the adult, flying stage, of *Aedes aegypti* mosquitoes. 20 to 30 adult mosquitoes were placed in a 50 mL beaker covered with gauze and containing a cotton ball which had been wetted with one mL of 1% sucrose solution. After approximately 24 hours, the mosquitoes began to drink the sugar water containing toxin and were then dead 4-6 hours later. No mosquitoes died in a water-only control.

*Xenorhabdus* MT is grown in either complex medium (such as in Nutrient broth, 20 grams peptone extract or 30 grams meat extract in 1 liter water) or in defined salts medium with 0.1 M carbon source including, but not limited to, glucose or glycerol and a vitamin source. Viable cells can be preserved using standard microbiological methods, for example lyophilization or with storage in glycerol at −80° C.

For mosquitocidal toxin production, either complex medium or defined medium can be used for culture for about 2-3 days at 30° C. with aeration, at least until stationary phase is reached.

TABLE 1

Production of mosquitocidal activity by *Xenorhabdus* sp

| Media | Time (da) | Temperature | MLD |
|---|---|---|---|
| 2% nutrient broth | 1 | 30 | 0 |
| | 2 | 30 | 25 |
| | 3 | 30 | 10 |

TABLE 1-continued Production of mosquitocidal activity by *Xenorhabdus* sp

| Media | Time (da) | Temperature | MLD |
|---|---|---|---|
|  | 5 | 30 | 10 |
|  | 14 | 30 | 10 |
|  |  |  | 10 |
| 2% nutrient broth | 3 | 25 | 25 |
|  | 3 | 35 | 25 |
|  | 3 | 37 | 0 |
| 2% Bacto peptone | 3 | 30 | 25 |
| 2% Proteose peptone | 3 | 30 | 25 |
| 2% Nutrient broth + 50 mM glucose | 3 | 30 | 10 |
| MS + glucose | 3 | 30 | 5 |
| MS + glycerol | 3 | 30 | 5 |

MLD μl growth liquor causing 100% lethality of 15-20 *A. aegypti* larvae after 24 hr. incubation; MS: 25 mM Na—K phosphate pH 7; 0.25 mM $(NH_4)_2SO_4$, 100 mM carbon source and trace amounts of vitamins (or nicotinamide) or yeast extract; Cultures shaken at 180 rpm.

Approximately half the mosquitocidal activity is cell-associated (and/or associated with the wall-membrane fraction of disrupted cells) and about half is found in the spent medium. See Table 2 for further information. At least some of the active toxin can be removed from cells or cell debris using acid (0.01 N HCl), alkali (0.01 N NaOH) or salt (1 M NaCl) extraction.

TABLE 2

Location of *Xenorhabdus* mosquitocidal activity

|  | % Activity* |
|---|---|
| Live cells | 100 |
| Heat killed cells (90° C., 20 min) | 100 |
| Sonication disrupted |  |
| Supernatant | 0 |
| Pellet | 100 |
| French press disrupted |  |
| Supernatant | 0 |
| Pellet | 100 |
| 1.0M NaCl, 24 hr |  |
| Supernatant | 20 |
| Pellet | 80 |
| 0.01M HCl, 24 hr |  |
| Supernatant | 40 |
| Pellet | 60 |
| 0.01M NaOH, 24 hr |  |
| Supernatant | 90 |
| Pellet (cells lysed) | 10 |

*10 μl sample applied to 10-20 *A. aegypti* larvae in 0.5 mL and observed after 24 hours.

The mosquitocidal toxin produced as described herein above has been purified to apparent homogeneity using the scheme shown in Table 3.

Figure 2:
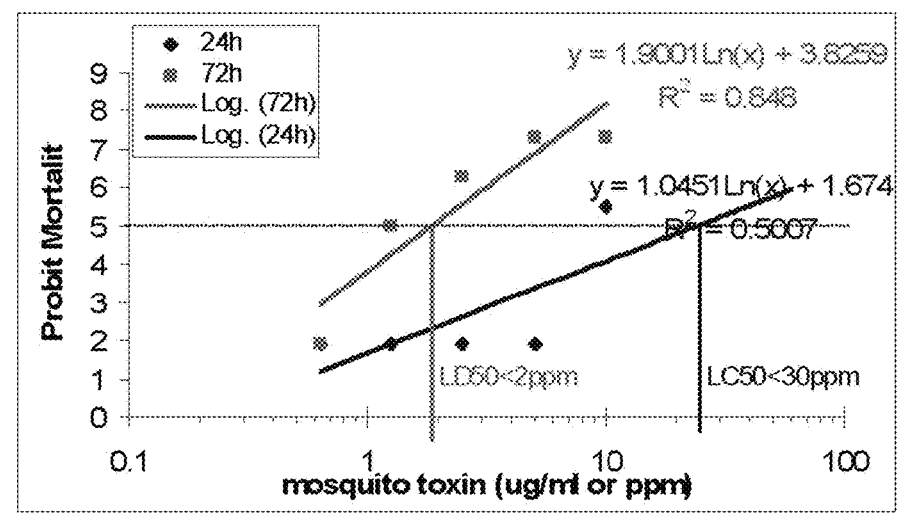

Assays were carried out for both mosquitocidal activity and for activity against larvae of the lepidopteran insect *Manduca sexta* (tobacco horn worm). The results are shown in Table 5. The growth liquor (supernatant after removal of cells by centrifugation) contained toxicity for both test insects. All of both activities were precipitated from growth liquor using three volumes of acetone, a procedure that concentrates the preparation by 40 fold. The acetone precipitate was dried to remove residual acetone and then dissolved in water and applied to a 2.0 by 30 cm column of the anion exchange matrix Sepharose™ Q. The mosquitocidal activity was not absorbed, indicating that the toxin is positively charged. The *M. sexta* activity was completely absorbed by the resin and was eluted with 0.5M NaCl. This is an important purification step that separates the lepidopteran (*Manduca*) and mosquito killing activities. The flow through fraction not absorbed by the resin was concentrated in vacuo to 10 mL and applied to a 1.0×5.0 cm CM (carboxy methyl) Sepharose™ cation exchange column. The activity was completely absorbed by the resin and was eluted using 1.0M NaCl. This eluate was next separated by reverse phase high pressure liquid chromatography (HPLC) using a preparative 1.0×20 cm C18 column and elution with a acetonitrile 0.1% trifluoroacetate gradient. FIG. 2 shows that the activity was eluted from the column as a series of peaks absorbing at 215 nm (the toxin has no absorbance at 280 nm) appearing between 40 and 55 minutes. Materials from each of these peaks were mosquitocidal. The material in each two milliliter fraction, from 40 to 55 minutes elution, was individually purified further by HPLC. The molecular weights of the eluted fractions, now with a single predominant band of absorbance, were determined by MALDI-TOF mass spectroscopy. Representative results of the mass spectra data are shown in Table 4. These results show that the XLT is comprised of a series of peptide molecules varying in size from 1182 to 1478 Da.

Total amino acid analyses of XLT performed by the Molecular Structure Facility, University of California Davis, revealed the toxin to be comprised of 2 histidine residues, 3 asparagine/aspartate residues, and 1 residue each of 2,3-diaminobutyric acid, glycine and serine. Fatty acid analyses of methyl derivatives of two samples of acid-hydrolyzed XLT, obtained from two HPLC peak fractions, revealed one sample contained 2-oxodecanoic acid and the other 2 oxo-octadecanoic acid. These analyses confirm that XLT is a lipopeptide with variable fatty acid constituents.

TABLE 3

Purification of *Xenorhabdus* mosquito toxin

| | mLd* | |
| Fraction | *Manduca sexta* | *Aedes aegypti* |
|---|---|---|
| Growth liquor | 1000 | 25 | 10 |
| 3:1 acetone precipitate | 25 | 100 | 2 |
| Sepharose ™ Q |  |  |  |
| Flow through | 40 | 0 | 10 |
| NaCl eluted | 25 | 100 | 0 |
| Sepharose ™ CM |  |  |  |
| 1.0M NaCl eluted | 10 | 0 | 2 |
| C18 reverse phase HPLC |  |  |  |
| Sepharose ™ Q Pool active fractions | 10 | 0 | 2 |

*μL sample showing 80-100% lethal effect after 24 hr *Aedes*, 5 days *Manduca*; *M sexta*: μL test sample added to 1 cm food source, 10 larvae tested; *A. aegypti*: μL test sample added to 10-20 larvae in 0.5 mL water

TABLE 4

Sizes of mosquitocidal peptides produced by
*Xenorhabdus innexi scapterisci*

| Elution time (min) | Toxicity* | Molecular weights (Da)** Major | Minor |
|---|---|---|---|
| 40-42 | + | 1306 | 1350 |
| 42-44 | + | 1350 | 1392 |
| 44-46 | + | 1350 | 1392 |
| 46-48 | + | 1363 | 1349 |
| 48-50 | + | 1195 | 1209 |
| 50-52 | + | 1195 | 1209 |
| 52-55 | + | 1197 | 1182 |
| 55-60 | + | 1478 | 1182 |

*80-100% of *Aedes aegypti* larvae killed in 24 hr, 10 μL sample;
**MALDI-TOF mass spectrometry, molecular weight estimates are plus or minus 3.

Stability properties of the crude preparations (spent medium) and purified preparations of mosquitocidal toxin have been studied, with measurements of activity made using the assay described herein.

There was no loss of activity for either toxin present in crude spent medium (growth liquor) or purified toxin with heating to 100° C. for 60 min or with heating at 120° C. (autoclaving) for 30 min. In addition, the toxic activity was maintained in dried preparations held at 25° C. for at least 36 months or at least 48 months at 0° C. In addition, this *Xenorhabdus* mosquitocidal toxin was stable to irradiation of an aqueous solution using an ultraviolet lamp (254 nm) for at least 2 hours. Finally, mosquitocidal activity was not decreased by exposure to proteases including trypsin, chymotrypsin, protease K, pronase or papain. Similarly, exposure to pH 1.0 or pH 10.5 for at least 24 hrs at 25° C. did not result in a significant change in activity.

Peptidome Comparison with Other *Xenorhabdus* and *Photorhabdus* Strains

The peptide spectrum of *Xenorhabdus* MT obtained by MALDI-TOF analysis was compared to those of certain other *Xenorhabdus* and *Photorhabdus* strains with antibiotic and/or mosquitocidal activity. The results are shown in Table 5. Note that none of the isolates produced the peptides characteristic of the mosquitocidal activity of *X. innexi* MT.

TABLE 5

Relevant Peptidomes of Selected *Xenorhabdus*
and *Photorhabdus* isolates (major components)

| Isolate | Mosquitocidal Activity[1] | Antibiotic Activity[2] | Peptide (Daltons) |
|---|---|---|---|
| *X. scapterisci innexi* | + | + | 1306, 1350, 1392 |
| *X. innexi* DSM | − | + | 1233, 1247, 1249 |
| *X. bovenii* | − | + | 1080, 1113, 1127, 1151 |
| *X. riobravis* | w | + | 1080, 1094, 1108, 1296 |
| *X. nematophilus* | w | + | 1080, 1107, 1130 |
| *X. japonica* | − | + | 1080, 1094, 1108, 1130 |
| *P. luminescens* tto 1 | w | + | 1097, 1389 |
| SLP[3] | + | + | 1199, 1213, 1462, 1519 |
| XNH3[3] | w | + | 1075, 1113, 1127, 1131 |
| SEX20[3] | + | + | 1105, 1162, 1185, 1901 |
| MP4[3] | − | + | 1213 |
| SEP389[3] | − | + | 1105, 1162, 1518, 1590 |
| SEP301[3] | w | + | 1105, 1340, 1354 |
| SEP562[3] | + | + | 1199, 1213, 1462, 1519, 1590 |
| GLX120[3] | w | + | 1389 |

[1] + (25 μl supernatant lethal to 15-20 *A. aegypti* larvae in 24 hr); w (50 μl supernatant lethal 72 hr); − (50 μl supernatant not lethal 72 hr);
[2] No growth of *Bacillus subtilis* or *Staphylococcus aureus*, 1.0 mL supernatant added to 25 mL culture;
[3] Isolated by J. Ensign; molecular weight estimates are plus or minus 3.

Structural Analysis of the Mosquitocidal Lipopeptide

The structure of the mosquitocidal lipopeptide was deduced using mass spectrometry data after hydrolysis of the lipopeptide. The mass spectral analysis was preceded by a standard vapor-phase acid hydrolysis to liberate the free amino acids, followed by (a) direct MS analysis of the free amino acids in the hydrolysate, and (b) derivatization with FDAA followed by LC/MS to help determine chirality, and to determine the amino acid residue masses in order to identify the various amino acids. These data were correlated to the direct infusion MS mass data to confirm the presence of the suspected amino acids. Without wishing to be bound by any particular theory, the amino acids in the *Xenorhabdus* XT are believed to include histidine, glycine, asparagine (and/or aspartate), diaminobutyric acid and serine, and there is at least one oxo-fatty acid of $C_8$ to $C_{20}$.

Mode of Action of *Xenorhabdus* Mosquito Toxin

The mode of action of the *Xenorhabdus* MT mosquito toxin (XLT) was studied in a mosquito larvae bioassay, modified from that of Addullah et al. (2003) Appl. Environ. Microbiol. 69: 5343-5374. Mosquitoes are reared in an environment-controlled room at 28° C. and 85% humidity, with a photoperiod of 14 h of light and 10 h of dark. Second-third instar larvae are used for all bioassays. Bioassays are performed 2-4 days after hatching of the larvae. A total of 10-20 larvae per 0.5 mL of water with one replicate in a 24-well Costar cell culture plate (Corning) were fed serial dilutions of the XLT preparations or defined amounts of the XLT preparations, and the mortality is counted after 24 hr incubation at 28° C.

The minimum lethal dose of XLT for *Aedes aegypti* larvae was determined as follows. Ten to twenty 3 to 4 instar *A. aegypti* larvae are placed in 0.5 mL water in wells of a 24 well microtiter plate. Serial dilutions of XLT were then added as 10 μL samples. After 8 and 24 hr incubation at 25° C. the numbers of live (motile) and dead (immotile) larvae were counted. The minimal lethal dose where all mosquitoes were killed was 10 μg of purified toxin.

Preparations of crude growth liquor and the purified XLT that were 100% lethal to *A. aegypti* larvae were equally effective in killing larvae of *Culex* and *Anopheles* mosquitoes.

TABLE 6

Lethal dose of XLT toxin for $3^{rd}$ instar *Aedes aegypti* larvae

| Micrograms toxin | Percent of Mosquitoes Live | Dead |
|---|---|---|
| 1000 | 0 | 100 |
| 500 | 0 | 100 |

TABLE 6-continued

Lethal dose of XLT toxin for 3rd instar *Aedes aegypti* larvae

| Micrograms toxin | Percent of Mosquitoes | |
|---|---|---|
| | Live | Dead |
| 250 | 0 | 100 |
| 100 | 0 | 100 |
| 50 | 0 | 100 |
| 25 | 0 | 100 |
| 10 | 10 | 90 |
| 5 | 100 | 0 |
| 0 | 100 | 0 |

15-20 third instar *Aedes aegypti* larvae in 0.5 mL water. Samples of HPLC purified XLT added and numbers of live and dead larvae counted after 23 hours incubation at 25° C.

The action of XLT was assessed in cell cultures as follows. *A. aegypti* cell line Aag2 was propagated in Eagle Medium supplemented with 5% bovine fetal serum (BFS), and *Manduca sexta* cell line GV1 was propagated in Grace Medium supplemented with 10% BFS.

Figure 3:
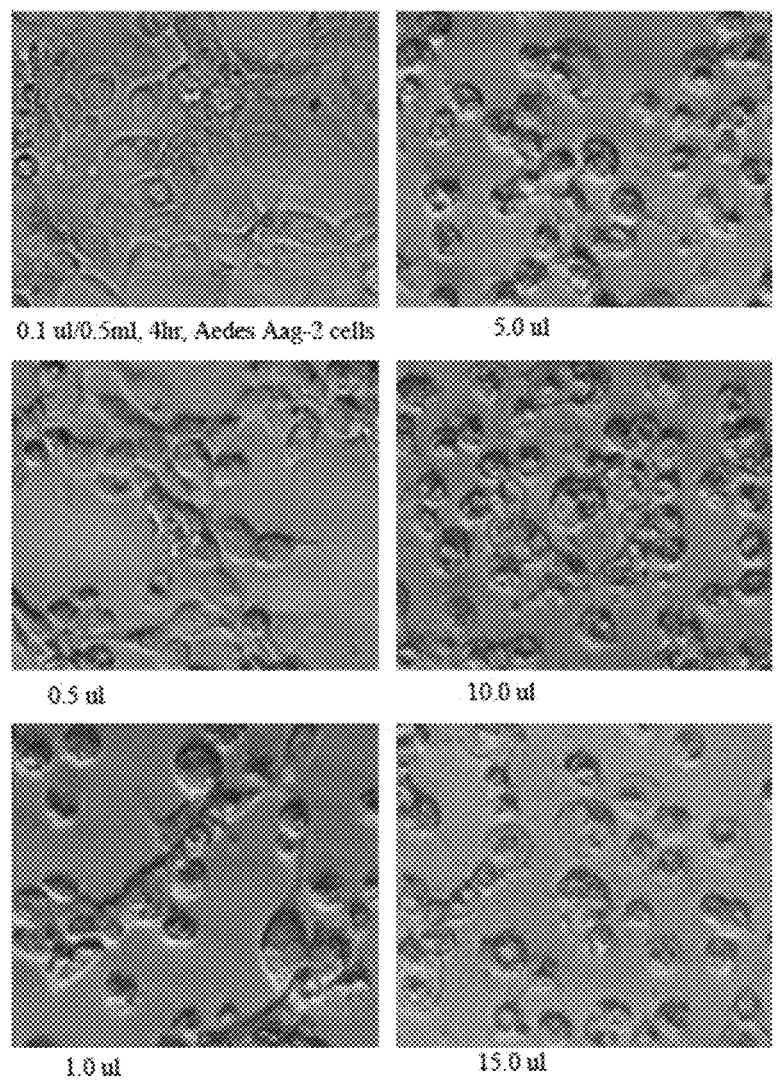
FIG. 3 shows the response of cultured *A. aegypti* cells to different amounts of the *Xenorhabdus* mosquitocidal toxin.
Figure 4:
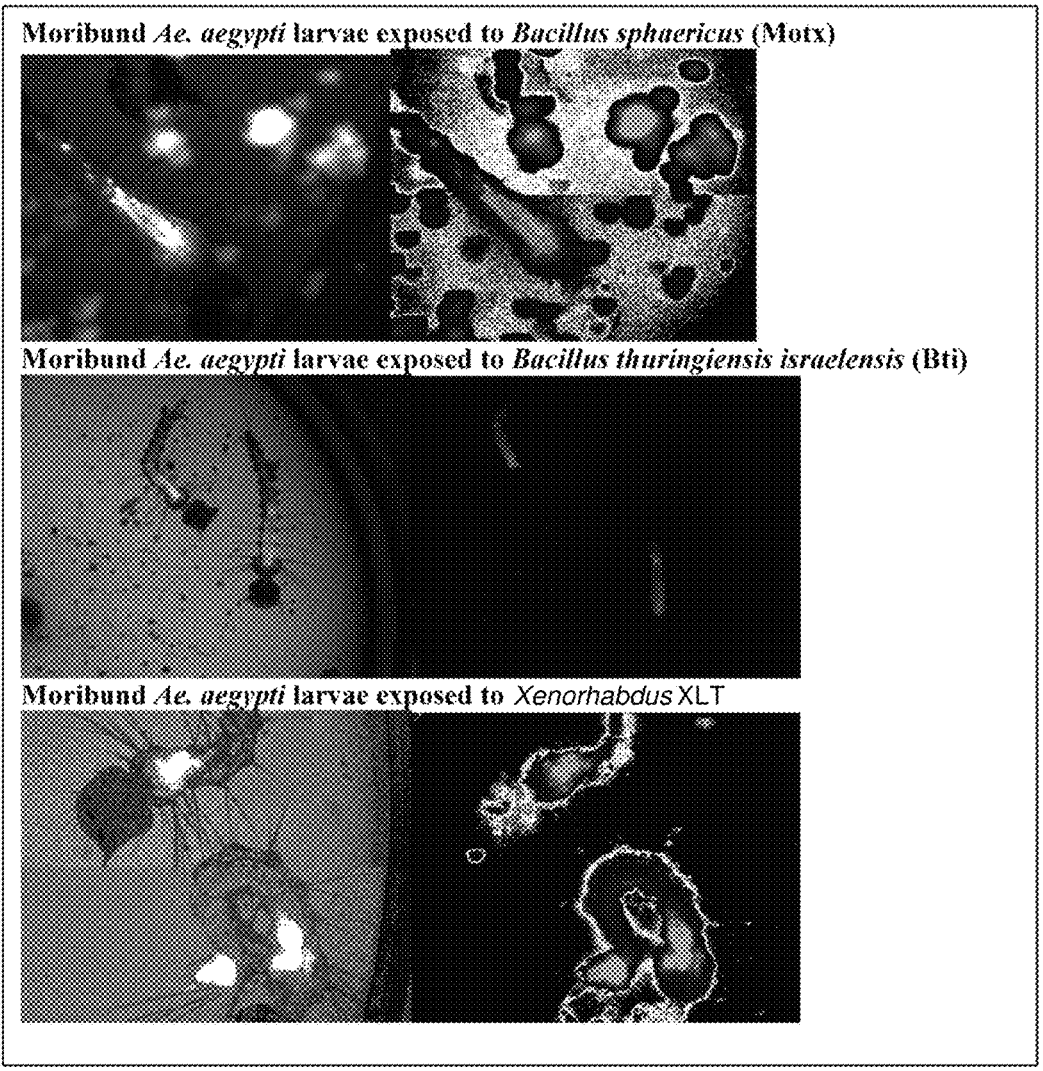
FIG. 4 shows the appearance of *A. aegyptii* larvae exposed to a mosquitocidal toxin from *B. sphaericus*, to a mosquitocidal toxin from *B. thuringiensis* israeliensis and to the mosquitocidal toxin from the *Xenorhabdus* MT (on the left) and the same larvae, stained with SYTOX™ green on the right.
Figure 5A:
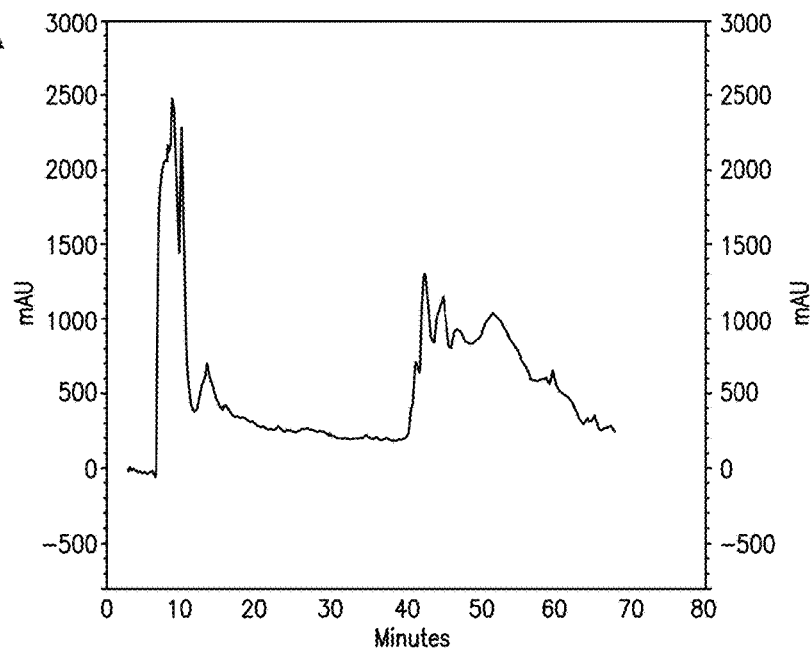
FIG. 5A-5B depicts chromatographic separation of XLT from other bacterial products.
Figure 5B:
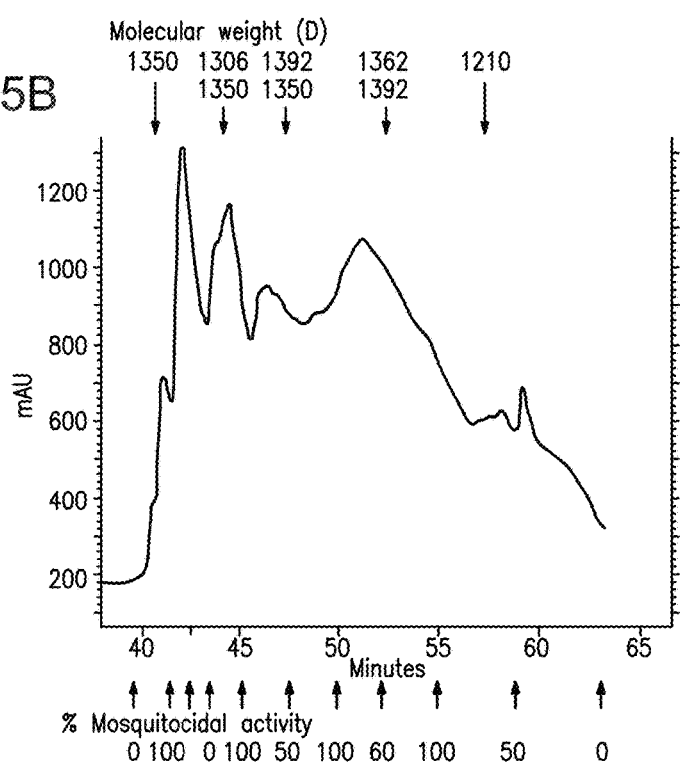

1 mL aliquots of cells (at a cell density of $5 \times 10^5$ cells/mL) were seeded in individual wells in a 24-well cell culture plate. Cells were allowed to grow overnight at 28° C. and 26° C., for Aag-2 and GV1, respectively. Cells were treated with XLT by adding 5 µl of HPLC purified toxin into the 1 mL culture aliquots in wells. After 24 hours of incubation, the cells were observed microscopically. The results are shown in FIG. 3.

*A. aegyptii* Aag-2 cells showed clear symptoms of XLT cytotoxicity after 24 hrs, All Aag-2 cells were lysed by XMT resulting in loss of viability. *M. sexta* GV1 cells showed slight morphological changes after the 24 hr incubation after exposure to XLT, but the cells remained viable. Therefore, under similar conditions, mosquito cells were significantly more sensitive to the cytotoxic action of XLT.

The mode of action of XLT toxin was also studied in intact larvae. *A. aegypti* $2^{nd}$ instar larvae were treated with HPLC-purified XLT at 10 µl and 100 µl in the presence of 8 µM SYTOX™ Green (Invitrogen, Carlsbad, Calif.), 5 larvae/well in a 96 well microtiter plate. SYTOX™ Green stains the DNA of dead cells, but living cells exclude SYTOX™ Green and thus are do not show staining. The larvae were observed under a fluorescent microscope (with green filter) after allowing access to the XLT toxin for 2 hours. Cell death was detected within 2 hours of access. Two other bacterial mosquito toxins were used as controls (the insecticidal *B. thuringiensis israeliensis* (Bti) toxin and *Bacillus sphaericus* mosquitocidal toxin Motx that are known to kill mosquito larvae via actions in the midgut).

In both Bti- and Motx-treated larvae, initial cellular death occurred in the midgut, as evidenced by intense green fluorescent staining in the midgut, which is consistent with the known mode of action of Bti and Motx. In the XLT-treated larvae, however, initial cell death occurred in the foregut and the hindgut regions, indicating that the mode of action of XLT toxin is different from the other known bacterial mosquito toxins.

Additional Method for Preparing XLT

The major difference from the protocol disclosed above is that the above protocol results in isolation of the individual components differing in the fatty acid component(s), while this (large scale protocol) results in a single product containing all the fractions and is adaptable to larger volumes of material. For use of the toxin on an industrial scale or for insect control, no purification is necessary and whole entire culture (including cells) can be applied.

A single isolated blue colony from LB plate containing 0.004% (w/v) triphenyl tetrazolium chloride and 0.025% (w/v) bromothymol blue is inoculated into 10 mL Mineral Salt Medium (0.05M $Na_2HPO_4$—$KH_2PO_4$ at pH 7.0, 0.02M $(NH_4)_2SO_4$, 0.001 M $MgSO_4$, 1% yeast extract) containing 0.1 M glucose, and it is incubated with shaking at 220 rpm at 30° C. for overnight, or 16-24 hrs, advantageously about 15-16 hrs, to produce a starter culture. A 1 mL aliquot is centrifuged and the mosquito larvicidal activity is confirmed using 10 µl of the starter culture supernatant.

After 6-12 hours, when the larvicidal activity has been confirmed, the starter culture is inoculated into two 2 liter flasks each containing 500 mL Mineral Salt Medium (0.05M $Na_2HPO_4$—$KH_2PO_4$ at pH 7.0, 0.02M $(NH_4)_2SO_4$, 0.001 M $MgSO_4$, 1% yeast extract) containing 0.1 M glucose, and the cultures are incubated shaking at 220 rpm at 30° C. for 72 hours. The culture is then centrifuged at 6,000 rpm for 20 minutes. The supernatant is collected for purification.

The XLT is then purified from the approximately one liter of culture supernatant by reversed phase/C18 column purification using a 8×40 cm Reveleris™ C18 Reverse-Phase 120 g Cartridge (Grace Davison Discovery Sciences, Deerfield, Ill. (Pump P-1, Amersham Bioscience). The column is pre-washed with 500 mL of 10% Acetonitrile/water with 0.1% trifluoroacetic acid (AN-TFA) at 5 mL/min flow rate, delivered using a peristaltic pump. The column is then loaded with 1-liter of culture supernatant at a 5 mL/min flow rate. Then the column is washed with 300 mL 10% AN-TFA at a flow rate of 5 mL/min, then washed with 500 mL 25% AN-TFA at a flow rate of 5 mL/min; washed with 100 mL 30% AN-TFA at a flow rate of 5 mL/min; washed with 100 mL 40% AN-TFA at 5 mL/min, collecting the eluted material containing the XLT.

The column is regenerated by washing with 300 mL 100% Acetonitrile at a flow rate of 5 mL/min; and then washed with 200 mL 10% AN-TFA at a flow rate of 5 mL/min. The column is then stored in 200 mL 80% AN-TFA.

The collected 40% AN-TFA sample is lyophilized overnight, or until dry. When dry, the sample is rehydrated with 20 mL of dd$H_2O$. The rehydrated material is filtered using a 0.22 µm membrane. Mosquito larvicidal assay is used to confirm activity, using 10 µl of the filtrate. After 3-6 hours, or after the larvicidal activity is confirmed, the filtrate is further purified using a HyperSep C18 SPE reverse phase column which has been preconditioned using 10% AN-TFA.

The 20 mL filtered sample is loaded onto the HyperSep C18 SPE reverse phase column. The column is subsequently washed using successive washed of 75 mL 10% AN-TFA and the flow-through material is discarded. XLT is eluted from the column with 75 mL 25% AN-TFA and 75 mL of 30% AN-TFA, and the eluates from each of these washes, containing the XLT, are collected. The column is then washed with 50 mL each of 50% AN-TFA and 100% AN-TFA to remove remaining material.

The 25% and 30% eluates are pooled and lyophilized overnight or until dry. The lyophilized samples are rehydrated with 15 mL of dd$H_2O$ and filtered using a 0.22 µm membrane filter.

A mosquito larvae assay is carried out with 10 µl of filtrate, and the filtrate containing the XLT is stored at 4° C.

If needed or desired, HPLC purification is carried out using a Reverse phase HPLC (System Gold Programmable Solvent Model 126, Beckman Coulter, Fullerton, Calif.) using a GRACE VYDAC Protein & Peptide C18 column (W.R. Grace & Co., Columbia, Md.). The column is eluted with distilled water with 0.1% trifluoroacetic acid (solvent A) and acetonitrile with 0.1% trifluoroacetic acid (solvent B). The eluant absorbance is monitored at 215 nm and 254 nm absorbance.

A gradient is set up so that solvent B increased from 0 to 20 percent over the first 20 minutes at a flow rate of 3 mL/min, and then 20 to 40 percent over 40 minutes at a flow rate of 2 mL/min.

The column is pre-washed with 10% solvent B at 2 mL/min flow rate for 40 minutes. Approximately 5 mL of samples are injected into the HPLC system. Approximately 2 mL fractions of samples are collected in clean microcentrifuge tubes as absorbance peaks appeared in chromatograms at 215 nm.

Once the run is completed, the column is washed with 100% solvent B for 40 minutes at a flow rate of 3 mL/min flow rate, and then washed again with 10% solvent B for 1 hour at a flow rate of 2 mL/min.

The collected fractions are tested for mosquito larvicidal activity and then pooled together by peaks appeared on the chromatogram.

The pooled collected samples are dried or concentrated using a SpeedVac Concentrator at room temperature (overnight or as needed). The dried material is resuspended with 200 µl of deionized water.

Antimicrobial Activity

The XLT compounds disclosed herein also exhibit potent antimicrobial activity, against Gram positive and Gram negative bacteria as well as against a representative fungal pathogen. *X. innexi scapterisci* was grown in defined medium supplemented with glucose and 0.1% yeast extract broth (as for the mosquitocide) at 30° C. 1.0 mL samples removed daily for 10 days, and the samples were centrifuged. The cell free supernatant was tested for antimicrobial activity by adding 5, 10, 25 and 50 µL to microtiter plate wells each containing 200 µl of suspension of test organism in 2% nutrient broth. The plate was then incubated at 37° C. for 18 hr, and turbidity of wells was read in a microtiter plate reader at 550 nm.

These XLT compounds are useful as antimicrobial agents and in methods for inhibition of microbial growth using the XLT(s) produced by *X. innexi scapeterisci*, deposited with the ATCC as PTA-6826. The antibiotic activity co-purifies with the mosquitocidal activity. Each individual HPLC peak has both antimicrobial and mosquitocidal activities.

Antimicrobial activity was assessed in in 0.3 mL microtiter wells. Each mL of broth was inoculated to contain approximately 100,000 cells/mL. The lethal dose (complete inhibition of growth at 24 hr) for all bacteria tested except *P. aeruginosa* was 0.13 µg/mL (130 ng/mL). For *P. aeruginosa*, the lethal dose was 0.26 ng/mL. The minimal lethal doses were determined using fully purified toxin-antibiotic (XLT) using microtiter plate assays with dilutions of HPLC fractions, where concentration of XLT was determined by measuring optical density at 215 nm using a microdrop reader. These assays included the *Salmonella, Listeria* and *Campylobacter* strains.

These XLT materials disclosed herein have potent antimicrobial activities and are useful against bacteria including *Escherichia coli, Salmonella enteriditis, Salmonella typhimurium, Salmonella agona, Listeria monocytogenes, Staphylococcus aureus, Pseudomonas aeruginosa, Micrococcus luteus, Bacillus cereus*, and fungi including *Candida albicans*. These compounds are effective for use in human and/or veterinary medicine or as agents in agricultural, food science or industrial applications. Antimicrobial compounds of the present invention are also useful for inhibiting the microbial growth and for treating infections in humans or animals caused by those pathogens listed above and other microorganisms as well.

TABLE 7

Antimicrobial Activity of the *Xenorhabdus mosquitocidal* toxin material.

| | microliters supernatant showing 90-100% growth inhibition | | | | | |
|---|---|---|---|---|---|---|
| Time days | S. aureus | E. coli | P. aeruginosa | Bacillus cereus | Micrococcus luteus | Candida albicans (yeast) |
| 1 | 50 | 50 | ni | 50 | 50 | 50 |
| 2 | 5 | 10 | 25 | 5 | 5 | 5 |
| 3 | 5 | 5 | 10 | 5 | 5 | 5 |
| 5 | 5 | 5 | 10 | 5 | 5 | 5 |
| 10 | 5 | 5 | 10 | 5 | 5 | 5 | ni = no inhibition

Note *Pseudomonas aeruginosa* is slightly less susceptible than certain other organisms. The antimicrobial activity is very stable, as is the mosquitocidal activity, since both activities are mediated by the same microbial products.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. It is not intended that any peptides disclosed in the prior art, except in prior applications from which priority may be claimed herein, are to be included in the present claimed invention in the United States, but peptides in the prior art are to be excluded from claimed peptides in countries outside the United States where priority is not claimed to an application which describes same.

The invention has been described with reference to various specific and preferred embodiments and techniques. However, it should be understood that many variations and modifications may be made while remaining within the true spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. It is not intended, however, for any claim herein to specifically encompass any precise embodiment existing and legally qualifying in the relevant jurisdiction as prior art for novelty; a claim purportedly encompassing such an embodiment is intended to be of scope so as to just exclude any such precise embodiment.

Whenever a range is disclosed, all subranges and individual values are intended to be encompassed. This invention is not to be limited by the embodiments disclosed, including any shown in the drawings or exemplified in the specification, which are given by way of example or illustration and not of limitation.

All references throughout this application, including but not limited to patent documents, non-patent literature documents and other source materials; are hereby incorporated by reference herein, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification reflect the level of skill of those skilled in the art to which the present methods and compositions pertain. References cited herein are incorporated by reference herein in their entirety to indicate the state of the art, and it is intended that this information can be employed herein, if needed, to exclude (for example, to disclaim) specific embodiments that are in the prior art. For example, when a compound is claimed, it should be understood that compounds known in the prior art, including any compounds or methods disclosed in the references cited herein (particularly in referenced patent documents), are not intended to be included in the claimed subject matter.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, synthetic methods and bacterial strains other than those specifically exemplified can be employed in the practice of the invention without resort to undue experimentation. All art-known functional equivalents, of any such methods, starting materials, synthetic methods and bacterial strains are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

In the context of this application, insecticidal means that exposure to or consumption of the *Xenorhabdus* lipopeptide toxin described herein results in the death of at least one insect, especially of at least one insect larva.

In the present application spent culture medium or a whole spent culture medium (including cells) is substantially synonymous with a fermentation broth or spent fermentations broth, in that it is the product of growth of *Xenorhabdus* MT (PTA 6826) or a strain which produces the same mosquitocidal lipopeptide and it contains that same mosquitocidal lipopeptide.

Recognition that the mosquitocidal lipopeptide toxin described herein acts in the gut of the mosquito larva, for example after oral ingestion, leads to the development of insect control compositions and methods which rely on ingestion in an infested environment. One way to introduce the mosquitocidal peptide described herein is in insect (especially mosquito) baits.

The mosquitocidal lipopeptide(s) may be administered to insects in either a purified or a nonpurified form, for example, in amounts from about 1 to about 1000 mg/liter of broth or other formulation. Where the compositions contain *Xenorhabdus* cells, the cells may be viable or nonviable. Insecticidal; formulations may be applied as dried powders or pellets or a liquid formulations, for example, by spraying. Whole or cell free spent fermentation broths may be dried or concentrated by suitable ultrafiltration methods, spray drying, drum drying, or lyophilization. Insecticidal compositions can be applied to the infested environment using track sprayers, syringe sprayers, crop dusters, manual dispersal of dry or liquid material, or the like, in mosquitocidally effective amounts, for example from 100 grams to 100 pounds per acre.

Wetting agents, emulsifying agents and spreaders may be added to the *Xenorhabdus* toxin-containing preparations designed for application to an environment in which control of mosquito populations is desired. Emulsifiers are known to the art, and they can include alkyl phenols, Tween™ 80, Sandovit., 9 D 207, Novémol, Pinolene 1882, Petro AG, Span 80, Colloidal X77, Triton N60, Triton X100, Triton GR7M, Triton 155, Atlox 848, Tween™ 20, Triton X45 V Atplus 448 F, Triton X114 B.t., Atplus 300 F, V Atlox 849, or Atlox 3404/849, among others. Additionally inert materials may be added for bulk, as known to the art. After drying, the dried material may be milled for ease of handling and dispersion in water.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art.

The exact formulation, route of administration and dosage of an antimicrobial XLT lipopeptide can be chosen by the individual physician in view of the patient's condition (see, e.g., Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions, or to successful treatment. Conversely, the attending physician would also know to adjust treatment to higher levels if the clinical response were not adequate (precluding toxicity). The magnitude of an administered dose in the management of the disorder of interest varies with the severity of the condition to be treated and to the route of administration. The severity of the condition may, for example, be evaluated, in part, by standard prognostic evaluation methods. Further, the dose and perhaps dose frequency also vary according to the age, body weight, and response of the individual patient. A program comparable to that discussed above also may be used in veterinary medicine.

Depending on the specific conditions being treated and the targeting or delivery method selected, such agents may be formulated and administered systemically or locally. Techniques for formulation and administration may be found in Alfonso and Gennaro (1995). Suitable routes may include, for example, topical, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the antimicrobial XLT peptide(s) of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions provided herein, in particular those formulated as solutions, may be administered parenterally, such as by intravenous injection. Appropriate therapeutically effective antimicrobial compositions can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Antimicrobial XLT lipopeptides intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in antimicrobial methods include compositions wherein the active ingredients are contained in an effective amount to achieve the intended purpose. Determination of the effective amounts is well within the capability of those skilled in the art, especially in light of the detailed disclosure provided herein.

In addition to the active ingredients, these antimicrobial pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions provided herein may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

When a group of substituents is disclosed herein, it is understood that all individual members of those groups and all subgroups, including any isomers and enantiomers of the group members, and classes of compounds that can be formed using the substituents are disclosed separately.

When a compound is claimed, it should be understood that compounds known in the art, including the compounds disclosed in the references disclosed herein, are not intended to be included within the claim. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, media, fermentation strategies, starting materials, synthetic methods, and purification methods other than those specifically exemplified can be employed in the practice of the invention without resort to undue experimentation. All art-known functional equivalents, of any such methods, media, fermentation strategies, starting materials, synthetic methods, and purification methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Although the description herein contains specific information and examples, these should not be construed as limiting the scope of the invention but as merely providing illustrations of some of the embodiments of the invention. One skilled in the art readily appreciates that the present invention is well adapted to carry out the objects and obtain the ends and advantages mentioned, as well as those inherent in the present invention. Thus, additional embodiments are within the scope of the invention and within the following claims.

The invention claimed is:

1. A method of controlling a mosquito of the genus Culex, Aedes or Anopheles comprising the step of feeding the mosquito an effective amount of a lipopeptide toxin having oral toxin activity against the mosquito, wherein the lipopeptide toxin comprises one or more lipopeptides each having a peptide of eight amino acids wherein the peptide contains two histidines, three asparatic acids and/or asparagines, one 2,3-diaminobutryic acid, one glycine and one serine and each peptide has one fatty acid group selected from a saturated straight chain fatty acid, a 2-oxo fatty acid, a 3-oxo fatty acid or a 4-oxo fatty acid, wherein the fatty acid has from 8 to 20 carbon atoms, wherein the lipopeptide toxin comprises lipopeptide molecules ranging in molecular weight from 1182 to 1478 daltons, and wherein the lipopeptide toxin is not contained in a nematode.

2. The method of claim 1, wherein the fatty acid group has from 10 to 18 carbon atoms.

3. The method of claim 1, wherein the lipopeptide toxin is in the form of a composition which further comprises an additional insecticidal component.

4. The method of claim 3, wherein the additional insecticidal component is a chemical or a biological insecticide.

5. The method of claim 4, wherein the biological insecticide is a bacterial insecticidal toxin, spinosyn, a plant insecticidal toxin or an insect virus.

6. The method of claim 5, wherein the biological insecticide is a bacterial insecticidal toxin produced by a *Bacillus thuringiensis* or a *Bacillus thuringiensis israeliensis* strain.

7. The method of claim 1, wherein the fatty acid group is selected from 2-oxo-fatty acid groups having 8 to 20 carbon atoms.

8. The method of claim 1, wherein the fatty acid group is selected from 2-oxo-fatty acid groups having 10 to 18 carbon atoms.

9. The method of claim 1, wherein said lipopeptide toxin is produced by a pure bacterial culture of *Xenorhabdus* MT deposited with the ATCC as PTA-6826.

10. The method of claim 1, wherein the lipopeptide is contained within a composition comprising dried whole culture of *Xenorhabdus innexi*, concentrated whole culture of *Xenorhabdus innexi*, dried cell-free medium from a culture of *Xenorhabdus innexi*, or concentrated cell-free medium from a culture of *Xenorhabdus innexi*.

11. The method of claim 10, wherein the lipopeptide is contained within a composition comprising dried whole culture of *Xenorhabdus innexi*, dried cell-free medium from a culture of *Xenorhabdus innexi*, or concentrated cell-free medium from a culture of *Xenorhabdus innexi*.

12. The method of claim 10, wherein the lipopeptide is contained within a composition comprising dried whole culture of *Xenorhabdus innexi*, or dried cell-free medium from a culture of *Xenorhabdus innexi*.

13. The method of claim 1, wherein the lipopeptide toxin is a mixture of lipopeptides ranging in molecular weight from 1182 to 1478 daltons.

14. The method of clam 1, wherein the lipopeptide toxin consists of a mixture of lipopeptide molecules ranging in molecular weight from 1182 to 1478 daltons.

15. The method of claim 1, wherein the lipopeptide toxin is produced by a *Xenorhabdus innexi* culture.

16. The method of claim 15, wherein the lipopeptide toxin is isolated from cell-free growth liquor of said culture by:
    precipitation from the liquor with acetone, removal of acetone from the acetone precipitate, forming a water solution of the precipitate from which acetone is removed; applying the water solution on an anion exchange column and collecting the flow through fraction from the column.

17. The method of claim 16, wherein the flow through fraction of the anion exchange column is applied to a cation exchange column and eluted with 1.0 M aqueous NaCl.

18. The method of claim 10, wherein the *Xenorhabdus innexi* is *Xenorhabdus* MT deposited with the ATCC as PTA-6826.

19. A method of controlling a mosquito of the genus Culex, Aedes or Anopheles comprising the step of feeding the mosquito an effective amount of a lipopeptide toxin having oral toxin activity against the mosquito, wherein the lipopeptide toxin is produced by a pure bacterial culture of the *Xenorhabdus* MT deposited with the ATCC as PTA-6826, and isolated from cell-free growth liquor of said culture by:
    precipitation from the liquor with acetone, removal of acetone from the acetone precipitate, forming a water solution of the precipitate from which acetone is removed; applying the water solution on an anion exchange column and collecting the flow through fraction from the column.

20. The method of claim 19, wherein the flow through fraction of the anion exchange column is applied to a cation exchange column and eluted with 1.0 M aqueous NaCl.

21. The method of claim 20, wherein the fraction eluted from the cation exchange column with 1.0 M aqueous NaCl is separated by reverse phase high pressure liquid chromatography with an acetonitrile/0.1% trifluoroacetic acid gradient.

22. The method of claim 21, wherein the lipopeptide toxin comprises peptide molecules ranging in molecular weight from 1182 to 1478 daltons.

23. The method of claim 22, wherein the lipopeptide toxin comprises one or more lipopeptides each having a peptide of eight amino acids wherein the peptide contains two histidines, three asparatic acids and/or asparagines, one 2,3-diaminobutryic acid, one glycine and one serine and each peptide has one fatty acid group selected from a saturated straight chain fatty acid, a 2-oxo fatty acid, a 3-oxo fatty acid or a 4-oxo fatty acid, wherein the fatty acid has from 8 to 20 carbon atoms.

24. The method of claim 22, wherein the lipopeptide toxin is a mixture of lipopeptides each having a peptide of eight amino acids wherein the peptide contains two histidines, three asparatic acids and/or asparagines, one 2,3-diaminobutryic acid, one glycine and one serine and each peptide has one fatty acid group selected from a 2-oxo fatty acid group having from 8 to 20 carbon atoms.

25. The method of claim 22, wherein the lipopeptide toxin is a mixture of lipopeptides each having a peptide of eight amino acids wherein the peptide contains two histidines, three asparatic acids and/or asparagines, one 2,3-diaminobutryic acid, one glycine and one serine and each peptide has one fatty acid group selected from a 2-oxo fatty acid group having from 10 to 18 carbon atoms.

26. A method of controlling a mosquito of the genus Culex, Aedes or Anopheles comprising the step of feeding the mosquito an effective amount of a lipopeptide toxin having oral toxin activity against the mosquito, wherein the lipopeptide toxin comprises one or more lipopeptides each having a peptide of eight amino acids wherein the peptide contains two histidines, three asparatic acids and/or asparagines, one 2,3-diaminobutryic acid, one glycine and one serine and each peptide has one fatty acid group selected from a saturated straight chain fatty acid, a 2-oxo fatty acid, a 3-oxo fatty acid or a 4-oxo fatty acid, wherein the fatty acid has from 8 to 20 carbon atoms, wherein the lipopeptide toxin is not contained in a nematode, and wherein the lipopeptide toxin is produced by a *Xenorhabdus innexi* culture and is isolated from cell-free growth liquor of said culture by:
    precipitation from the liquor with acetone, removal of acetone from the acetone precipitate, forming a water solution of the precipitate from which acetone is removed; applying the water solution on an anion exchange column and collecting the flow through fraction from the column.

27. The method of claim 26, wherein the flow through fraction of the anion exchange column is applied to a cation exchange column and eluted with 1.0 M aqueous NaCl.

28. The method of claim 26, wherein the lipopeptide toxin comprises lipopeptide molecules ranging in molecular weight from 1182 to 1478 daltons.

* * * * *